(12) United States Patent
Sokolov et al.

(10) Patent No.: US 12,153,068 B2
(45) Date of Patent: *Nov. 26, 2024

(54) ATOMIC-FORCE MICROSCOPY FOR IDENTIFICATION OF SURFACES

(71) Applicant: Trustees of Tufts College, Medford, MA (US)

(72) Inventors: Igor Sokolov, Medford, MA (US); Milos Miljkovic, Medford, MA (US)

(73) Assignee: Trustees of Tufts College, Medford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/370,923

(22) Filed: Sep. 21, 2023

(65) Prior Publication Data
US 2024/0012022 A1 Jan. 11, 2024

Related U.S. Application Data

(63) Continuation of application No. 17/980,667, filed on Nov. 4, 2022, now Pat. No. 11,796,564, which is a (Continued)

(51) Int. Cl.
*G01Q 30/04* (2010.01)
*G01N 33/49* (2006.01)
(Continued)

(52) U.S. Cl.
CPC ............ *G01Q 30/04* (2013.01); *G01N 33/493* (2013.01); *G01N 33/57488* (2013.01);
(Continued)

(58) Field of Classification Search
CPC ...... G01Q 60/34; G01Q 60/42; G06V 20/698; G01N 33/493; G01N 33/57488
(Continued)

(56) References Cited

U.S. PATENT DOCUMENTS 9,904,866 B1 2/2018 Noble
11,506,683 B2 * 11/2022 Sokolov ............ G06F 18/24323
(Continued)

FOREIGN PATENT DOCUMENTS

CN 103460039 A 12/2013
WO 2016198535 A1 12/2016
(Continued)

OTHER PUBLICATIONS

Kazuki Ito, et al. "Identification and Principal Component Analysis of Exosome Release Source Cells by Machine Learning of AFM Images", 2018 the 79th Japan Society of Applied Physics Autumn Meeting [Lecture Proceedings] Extended Abstracts of the 79th JSAP Autumn Meeting, 2018 , The Japan Society of Applied Physics, 2018, The Japan Society of Applied Physics, Sep. 5, 2018.
(Continued)

*Primary Examiner* — Nicole M Ippolito
(74) *Attorney, Agent, or Firm* — Occhiuti & Rohlicek LLP

(57) ABSTRACT

A method comprises using an atomic-force microscope, acquiring a set of images associated with surfaces, and, using a machine-learning algorithm applied to the images, classifying the surfaces. As a particular example, the classification can be done in a way that relies on surface parameters derived from the images rather than using the images directly.

11 Claims, 25 Drawing Sheets

Related U.S. Application Data continuation of application No. 17/291,430, filed as application No. PCT/US2019/060225 on Nov. 7, 2019, now Pat. No. 11,506,683.

(60) Provisional application No. 62/772,327, filed on Nov. 28, 2018, provisional application No. 62/756,958, filed on Nov. 7, 2018.

(51) Int. Cl.
| | |
|---|---|
| *G01N 33/493* | (2006.01) |
| *G01N 33/574* | (2006.01) |
| *G01Q 60/34* | (2010.01) |
| *G01Q 60/42* | (2010.01) |
| *G06V 10/764* | (2022.01) |
| *G06V 20/69* | (2022.01) |

(52) U.S. Cl.
CPC ............. *G01Q 60/34* (2013.01); *G01Q 60/42* (2013.01); *G06V 10/764* (2022.01); *G06V 20/698* (2022.01)

(58) Field of Classification Search
USPC .......................................................... 850/33
See application file for complete search history.

(56) References Cited

U.S. PATENT DOCUMENTS

| | | | |
|---|---|---|---|
| 11,796,564 B2* | 10/2023 | Sokolov | ................. G01Q 60/34 |
| 2008/0026410 A1 | 1/2008 | Vlahou | |
| 2014/0123347 A1 | 5/2014 | Gimzewski et al. | |
| 2015/0036889 A1 | 2/2015 | Ananda Yogendran | |
| 2015/0160225 A1 | 6/2015 | Ostroff et al. | |
| 2015/0292030 A1 | 10/2015 | McConkey et al. | |
| 2019/0331608 A1 | 10/2019 | Terasawa et al. | |

FOREIGN PATENT DOCUMENTS

| | | |
|---|---|---|
| WO | 2017216123 A1 | 12/2017 |
| WO | 2018134377 A1 | 7/2018 |

OTHER PUBLICATIONS

Nikiforov M P et al: "Functional recognition imaging using artificial neural networks: applications to rapid cellular identification via broadband electromechanical response", Nanotechnology, Institute of Physics Publishing, Bristol, GB, vol. 20, No. 40, Oct. 7, 2009 (Oct. 7, 2009), p. 405708, XP020164845, ISSN: 0957-4484, DOI: 10.1088/0957-4484/20/40/405708.

* cited by examiner

Algorithm Cancer Detection using Cell Surface Parameters

*function make_dataset()*   Inputs: CSV file, statistics parameter [mean or median]

Steps:
1) Load data from CSV file
2) Reject variables where all samples have the same value
3) Reject samples where data acquisition artifacts are present
4) Store data-frame with preprocessed data
5) Create data-frame with non-cancer samples with no cells
6) Merge preprocessed and non-cancer sample data-frames
7) Group samples by patient ID
8) Get mean or median values of all variables per cell, from cell quadrants, for all patient IDs and store in data-frame

Return: Cell samples data-frame

*function split_data_train_test()* Inputs: data-frame, train-test sample ratio Steps:
1) Split data-frame into training and testing samples, based on patient IDs, using selectable train-test sample ratio
2) Store training and testing samples data-frames

Return: training and testing samples data-frames

FIG. 11

*function make_classifier_model()* Inputs: model name, model parameters

Steps:
1) Select one of the following classification models: random forest, extra-trees, or gradient boosted trees
2) Specify selected model's parameters and instantiate the model

Return: Classification model object

*function classification_performance_metrics()* Inputs: classification model object, cell samples data-frame, M number of cells, N number of cells, R number of iterations Steps:

*for n-th run in R number of iterations:*
  run *make_classifier_model()*
  run *split_data_train_test()*
  1) Select M number of cells per patient ID to be used in measuring classification performance metrics for testing data-frame
  2) Select N number of cells per patient ID which need to be classified as cancer to classify the whole patient ID as cancer
  3) Using all cells available per patient ID, make all possible combinations of M cells for all patient IDs in the testing samples and store in data-frame
  4) Calculate model classification performance metrics: ROC curve, ROC AUC score, accuracy, and confusion matrix

Return: ROC curves, ROC AUC scores, accuracy scores, confusion matrices

FIG. 11 (cont.)

| | data | Random forest | | | Extremely Randomized Forest | | | Gradient Boosting Trees | | |
|---|---|---|---|---|---|---|---|---|---|---|
| | | AUC/Accuracy | Sense/spec | | AUC/Accuracy | Sense/spec | | AUC/Accuracy | Sense/spec | |
| N=1 | height | 75/73 | 50/84 | 76/69 | 77/74 | 53/84 | 77/70 | 74/73 | 46/86 | 75/68 |
| M=1 | adh. | 88/83 | 68/90 | 84/77 | 88/83 | 69/90 | 85/78 | 87/82 | 69/89 | 84/77 |
| N=2 | height | 75/77 | 40/91 | 76/69 | 77/78 | 44/91 | 77/71 | 75/77 | 40/92 | 75/69 |
| M=1 | adh. | 89/87 | 71/93 | 86/80 | 89/86 | 70/93 | 87/80 | 89/87 | 71/93 | 86/80 |
| N=2 | height | 77/78 | 43/92 | 76/69 | 78/79 | 48/91 | 78/71 | 75/78 | 38/93 | 74/68 |
| M=2 | adh. | 89/86 | 69/93 | 86/80 | 90/87 | 70/94 | 86/79 | 89/87 | 69/94 | 85/79 |
| N=3 | height | 73/81 | 34/95 | 75/66 | 74/81 | 35/95 | 76/67 | 73/81 | 35/95 | 74/66 |
| M=1 | adh. | 90/89 | 70/95 | 88/81 | 89/88 | 69/94 | 86/79 | 89/90 | 70/96 | 87/80 |
| N=3 | height | 75/82 | 36/95 | 75/68 | 78/82 | 42/94 | 77/69 | 73/81 | 34/96 | 73/66 |
| M=2 | adh. | 91/90 | 73/96 | 87/80 | 90/90 | 72/96 | 87/80 | 89/90 | 69/96 | 85/78 |
| N=3 | height | 75/82 | 37/95 | 76/67 | 78/83 | 42/95 | 77/69 | 72/81 | 32/96 | 73/66 |
| M=3 | adh. | 90/90 | 71/96 | 87/80 | 90/90 | 70/96 | 87/76 | 88/89 | 65/96 | 85/77 |
| N=4 | height | 69/84 | 31/97 | 71/61 | 70/84 | 33/97 | 73/64 | 69/84 | 34/97 | 73/64 |
| M=1 | adh. | 89/91 | 75/95 | 88/80 | 88/90 | 71/96 | 87/79 | 90/92 | 74/96 | 88/80 |
| N=4 | height | 72/84 | 35/97 | 73/64 | 74/85 | 37/96 | 76/67 | 71/84 | 37/96 | 72/63 |
| M=2 | adh. | 91/92 | 77/97 | 88/80 | 90/92 | 74/96 | 88/80 | 90/92 | 73/97 | 87/79 |
| N=4 | height | 72/84 | 34/97 | 74/64 | 76/85 | 41/96 | 76/67 | 70/84 | 32/97 | 71/62 |
| M=3 | adh. | 89/92 | 72/97 | 88/79 | 90/92 | 72/97 | 87/79 | 87/91 | 64/97 | 84/75 |
| N=4 | height | 72/84 | 32/97 | 74/64 | 75/85 | 38/96 | 76/66 | 70/84 | 32/97 | 72/62 |
| M=4 | adh. | 89/91 | 71/96 | 88/79 | 89/91 | 71/96 | 87/78 | 86/90 | 64/97 | 84/75 |
| N=5 | height | 66/86 | 33/98 | 69/57 | 66/85 | 36/97 | 72/60 | 67/86 | 35/98 | 70/59 |
| M=1 | adh. | 88/93 | 77/96 | 87/78 | 87/92 | 75/96 | 87/78 | 89/94 | 77/97 | 88/79 |
| N=5 | height | 69/86 | 34/97 | 72/61 | 70/86 | 39/96 | 76/64 | 68/86 | 36/97 | 70/61 |
| M=2 | adh. | 91/94 | 81/98 | 91/82 | 90/94 | 78/97 | 89/80 | 91/94 | 78/98 | 88/80 |
| N=5 | height | 68/86 | 31/98 | 72/61 | 72/87 | 39/97 | 76/65 | 67/86 | 34/97 | 69/58 |
| M=3 | adh. | 90/93 | 77/97 | 88/78 | 90/93 | 77/97 | 88/78 | 88/93 | 70/98 | 85/75 |
| N=5 | height | 67/86 | 34/97 | 72/60 | 72/87 | 39/97 | 76/64 | 65/85 | 30/97 | 69/57 |
| M=4 | adh. | 89/93 | 75/97 | 87/77 | 88/93 | 73/97 | 88/77 | 85/92 | 61/98 | 84/74 |
| N=5 | height | 68/86 | 30/97 | 72/59 | 74/87 | 39/97 | 76/63 | 67/85 | 32/97 | 71/59 |
| M=5 | adh. | 88/93 | 74/97 | 88/77 | 88/93 | 73/97 | 88/77 | 84/91 | 62/97 | 84/73 |

FIG. 21

ATOMIC-FORCE MICROSCOPY FOR IDENTIFICATION OF SURFACES

RELATED APPLICATIONS

This application is a continuation of U.S. application Ser. No. 17/980,667, filed Nov. 4, 2022, which is a continuation application of U.S. application Ser. No. 17/291,430, filed May 5, 2021, now U.S. Pat. No. 11,506,683, issued Nov. 22, 2022, which is a 371 application of International Application No. PCT/US2019/060225, filed Nov. 7, 2019, which claims the benefit of the Nov. 7, 2018 priority date of U.S. Provisional Application 62/756,958 and the Nov. 28, 2018 priority date of U.S. Provisional Application 62/772,327, the contents of which are incorporated herein by reference.

FIELD OF INVENTION

The invention relates to the use of atomic force microscopy and machine learning in connection with using features of a surface to classify or identify that surface, and in particular, to using features to identify or classify biological cells.

BACKGROUND

In atomic force microscopy, a probe attached to the tip of a cantilever scans the surface of the sample. In one mode for operation, the probe taps the surface as it scans. As the probe scans the sample, it is possible to control the magnitude and direction of the force vector associated with a loading force that the probe exerts on the sample.

The deflection of the cantilever from its equilibrium position provides a signal from which a great deal of information can be extracted. As an example, by keeping either the loading force or the cantilever's deflection constant, it is possible to obtain the sample's topology at various points on the sample. The values collected at each point are then organized into an array in which the row and column identifies the location of a point in a two-dimensional coordinate system and the value at the row and column is representative of a property measured at that point. The resulting array of numbers can thus be viewed as a map. This makes it possible to make a map of the sample in which each point on the map indicates some property of the sample's surface at that point. In some examples, the property is the height of the surface above or below some reference plane.

However, an image of the surface's height is not the only image that can be recorded when scanning. The cantilever's deflection can be used to collect multiple images of the sample's surface, with each image being a map of a different property of the surface. Examples of just a few of these properties include adhesion between the probe and the surface, the stiffness of the surface, and viscoelastic energy loss.

SUMMARY

The invention provides a method for identifying a surface using multidimensional images obtained by an atomic force microscope and for using information from those images for classifying a surface into one of several classes. According to the invention, it is possible to obtain a multi-dimensional image of a surface with two of the dimensions corresponding to spatial dimensions and additional dimensions corresponding to different physical and spatial properties that exist at the coordinate identified by the two spatial dimensions. In some embodiments, the dimensions are lateral dimensions.

A question that arises is how one chooses and uses these different physical and spatial properties for identification and classification of a surface. According to the invention, the properties that will be used for identification and classification of a surface are not pre-determined. They are calculated based on the result of machine learning applied to a database of images and their corresponding classes. They are learned. In particular, they are learned by machine learning.

Among the embodiments of the invention are those that include using an atomic force microscope to acquire different maps corresponding to different properties of the surface and using combinations of these maps, or parameters derived from those maps, to identify or classify a sample surface. Such a method comprises recording atomic force microscope images of examples of surfaces that belong to well-defined classes, forming a database in which such atomic force microscope maps are associated with the classes to which they belong, using the atomic force microscope maps thus obtained and the combinations thereof to learn how to classify surfaces by splitting the database into training and testing data with the training data being used to learn how to classify, for example by building a learning tree or neural network or a combination of thereof, and using the testing data to verify that the classification thus learned is effective enough to pass a given threshold of effectiveness.

Another embodiment includes reducing the maps provided by the atomic force microscope to a set of surface parameters, the values of which are defined by mathematical functions or algorithms that use those properties as inputs thereof. In a preferred practice, each map or image yields a surface parameter that can then be used as, together with other surface parameters to classify or identify the surface. In such embodiments, there exists a classifier that classifies based on these surface parameters. However, the classifier itself is not predetermined. It is learned though a machine-learning procedure as described above.

The method is agnostic to the nature of the surface. For example, one might use the method to classify surfaces of paintings or currency or secure documents such as birth certificates or passports in order to spot forgeries. But one might also use the same method to classify surfaces of cells or other portions of a living body in order to identify various disorders. For example, various cancers have cells that have particular surface signatures. Thus, the method can be used to detect various kinds of cancers.

A difficulty that arises is that of actually obtaining cells to examine. In some cases, an invasive procedure is required. However, there are certain kinds of cells that are naturally sloughed off the body or that can be extracted from the body with only minimal invasiveness. An example is that of gently scratching the cervix's surface in a Pap smear test. Among the cells that are naturally sloughed off are cells from the urinary tract, including the bladder. Thus, the method can be used to inspect these cells and detect bladder cancer without the need for an invasive and expensive procedure, such as cystoscopy.

The invention features using atomic force microscope that can produce a multidimensional array of physical properties, for example, when using sub-resonance tapping mode. In some practices, acquiring the set of images comprises using an atomic-force microscope in ringing mode to carry out nanoscale-resolution scanning of the surfaces of cells that have been collected from bodily fluids and providing data obtained from the atomic force microscope scanning procedure to a machine learning system that provides an indication of the probability that the sample came from a patient who has cancer, hereafter referred to as a "cancer-afflicted patient." The method is applicable in general to classifying cells based on their surface properties.

Although described in the context of bladder cancer, the methods and systems disclosed herein are applicable for detection of other cancers in which cells or body fluid are available for analysis without the need for invasive biopsy. Examples include cancer of the upper urinary tract, urethra, colorectal and other gastrointestinal cancers, cervical cancers, aerodigestive cancers, and other cancers with similar properties.

Moreover, the methods described herein are applicable to detection of cellular abnormalities other than cancer as well as to monitoring cellular reaction to various drugs. In addition, the methods described herein are useful for classifying and identifying surfaces of any type, whether derived from a living creature or from non-living matter. All that is necessary is that the surface be one that is susceptible to being scanned by an atomic force microscope.

For example, the method described herein can be used to detect forgeries, including forgeries of currency, stock certificates, identification papers, or artwork, such as paintings.

In one aspect, the invention features using an atomic-force microscope to acquire a set of images of each of a plurality of cells obtained from a patient, processing the images to obtain surface parameter maps, and, using a machine-learning algorithm applied to the images, classifying the cells as having originated in either a cancer-afflicted or cancer-free patient.

Among these embodiments are those in which the microscope is used in sub-resonance tapping mode. In yet other embodiments, the microscope is used in ringing mode.

In another aspect, the invention features: using an atomic-force microscope, acquiring a set of images associated with surfaces, processing the images to obtain surface parameter maps, and, using a machine-learning algorithm applied to the images, classifying the surfaces.

Among these practices are those that include selecting the surfaces to be surfaces of bladder cells and classifying the surfaces as those of cells that originated from a cancer-afflicted or cancer-free patient.

As used herein, "atomic forice microscopy," "AFM," "scanning probe microscopy," and "SPM" are to be regarded as synonymous.

The only methods described in this specification are non-abstract methods. Thus, the claims can only be directed to non-abstract implementations. As used herein, "non-abstract" is a deemed to mean compliant with the requirements of 35 USC 101 as of the filing of this application.

These and other features of the invention will be apparent from the following detailed description and the accompanying figures, in which:

BRIEF DESCRIPTION OF THE FIGURES

FIG. 11 shows a machine-learning method adapted to the data structure needed for classification;
FIG. 21 is a table showing statistics of the confusion matrix associated with cancer diagnosis for two separate channels, one of which is for height and the other of which is for adhesion.

DETAILED DESCRIPTION

Figure 1:
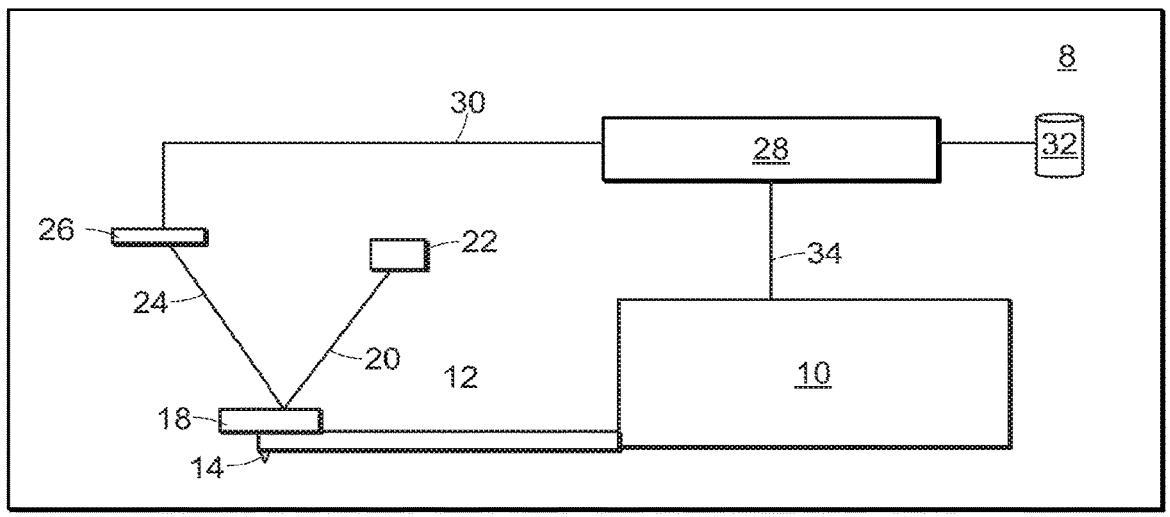
FIG. 1 shows a simplified diagram of one example of an atomic force microscope.

FIG. 1 shows an atomic force microscope 8 having a scanner 10 that supports a cantilever 12 to which is attached a probe 14. The probe 14 is thus cantilevered from the scanner 10. The scanner 10 moves the probe 14 along a scanning direction that is parallel to a reference plane of a sample's surface 16. In doing so the scanner 10 scans a region of a sample's surface 16. While the scanner is moving the probe 14 in the scanning direction, it is also moving it in a vertical direction perpendicular to the reference plane of the sample surface 16. This causes the distance from the probe 14 to the surface 16 to vary.

The probe 14 is generally coupled to a reflective portion of the cantilever 12. This reflective portion reflects an illumination beam 20 provided by a laser 22. This reflective portion of the cantilevered 12 will be referred to herein as a mirror 18. A reflected beam 24 travels from the mirror 18 to a photodetector 26, the output of which connects to a processor 28. In some embodiments, the processor 28 comprises FPGA electronics to permit real time calculation of surface parameters based on physical or geometric properties of the surface.

The movement of the probe 14 translates into movement of the mirror 18, which then results in different parts of the photodetector 26 being illuminated by the reflected beam 24. This results in a probe signal 30 indicative of probe movement. The processor 28 calculates certain surface parameters based on the probe signal 30 using methods described below and outputs the results 33 to a storage medium 32. These results 33 include data representative of any of the surface parameters described herein.

The scanner 10 connects to the processor 28 and provides to it a scanner signal 34 indicative of scanner position. This scanner signal 34 is also available for use in calculating surface parameters.

Figure 2:
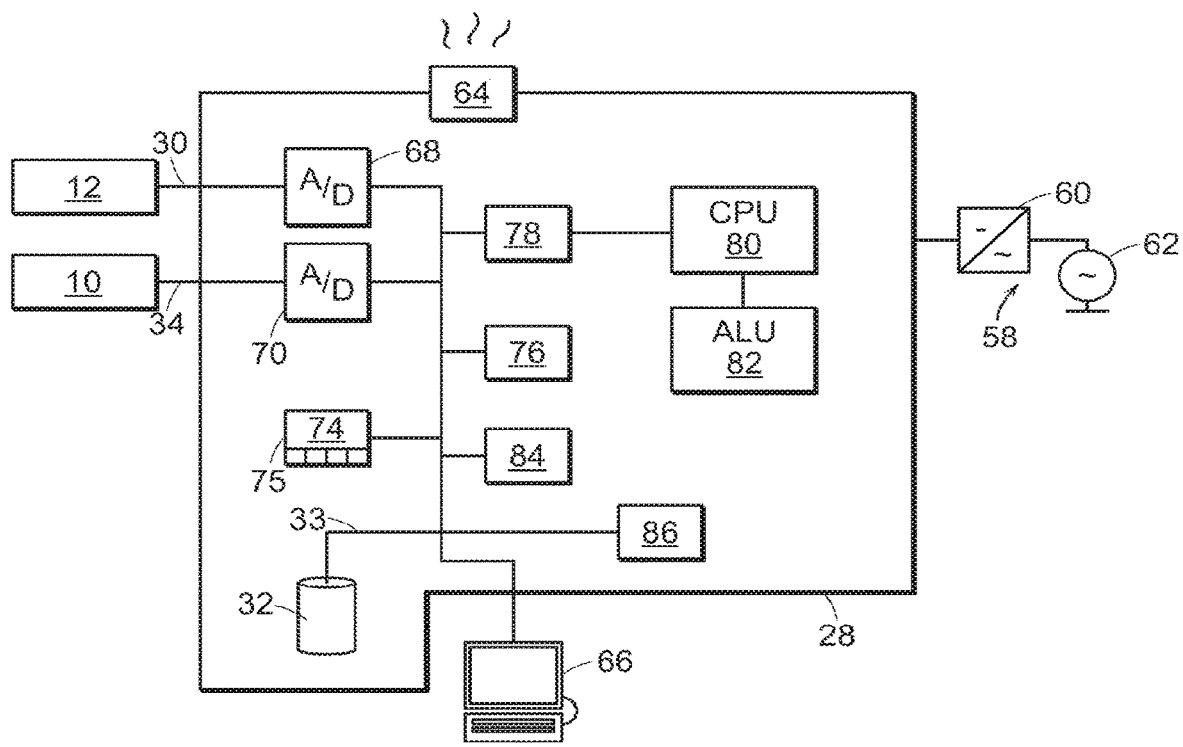
FIG. 2 shows additional details from the processing system of FIG. 1.

FIG. 2 shows the processing system 28 in detail. The processing system 28 features a power supply 58 having an AC source 60 connected to an inverter 62. The power supply 58 provides power for operating the various components described below. The processing system further includes a heat radiator 64.

In a preferred embodiment, the processing system 28 further includes a user interface 66 to enable a person to control its operation.

The processing system 28 further includes first and second A/D converters 68, 70 for receiving the probe signal and the scanner signals and placing them on a bus 72. A program storage section 74, a working memory 76, and CPU registers 78 are also connected to the bus 72. A CPU 80 for executing instructions 75 from program storage 74 connects to both the registers 78 and an ALU 82. A non-transitory computer-readable medium stores these instructions 75. When executed, the instructions 75 cause the processing system 28 to calculate any of the foregoing parameters based on inputs received through the first and second A/D converters 68, 70.

Figure 6:
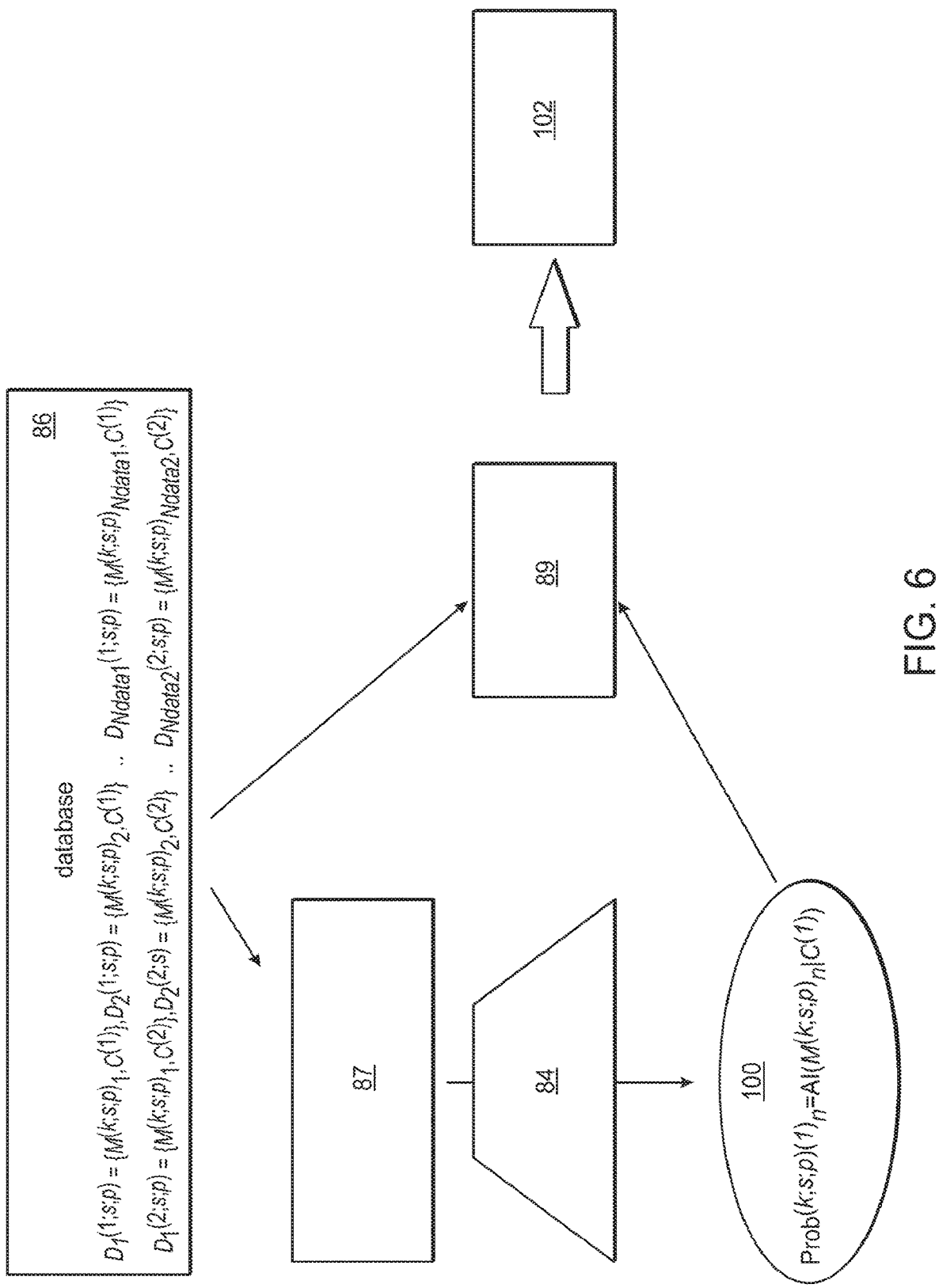
FIG. 6 shows details of interactions between the database and the machine-learning module in the processing system of FIG. 2.

The processing system 28 further includes a machine-learning module 84 and a database 86 that includes training data 87 and testing data 89, best seen in FIG. 6. The machine-learning module 84 uses the training data 87 and the testing data 89 for implementing the method described herein.

A specific example of the processing system 28 may include FPGA electronics that includes circuitry configured for determining the values of the properties of the imaging services and/or the surface parameters described above.

Figure 3:
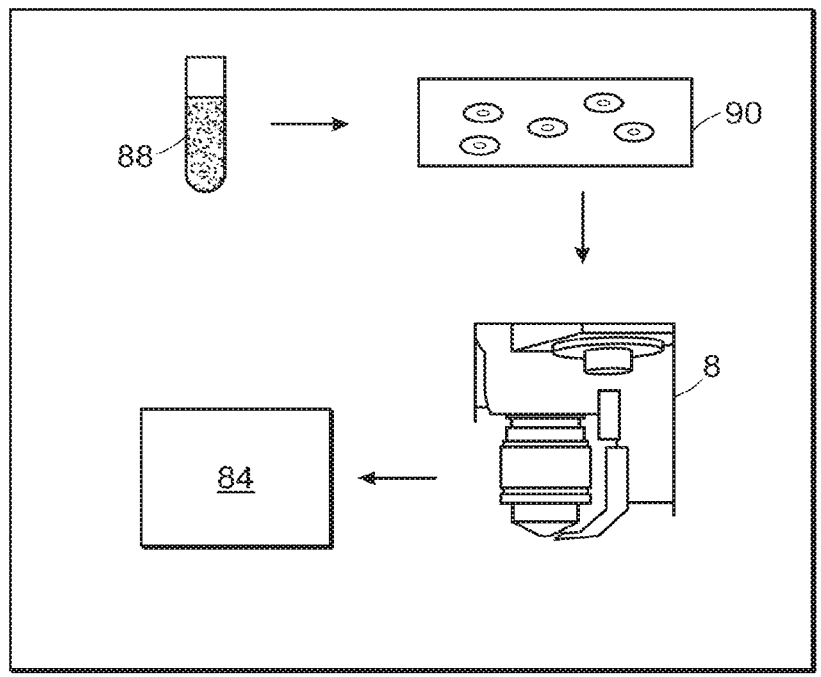
FIG. 3 shows a diagnostic method carried out by the atomic force microscope and the processing system shown in FIGS. 1 and 2.

FIG. 3 shows a process that uses an atomic force microscope 8 to acquire images and to provide them to the machine-learning module 84 to characterize the sample using the images. The process shown in FIG. 3 includes acquiring urine 88 from a patient and preparing cells 90 that have been sloughed off into the urine 88. After having scanned them, the atomic force microscope 8 provides images of the bladder cells 90 for storage in the database 86.

Each image is an array in which each element of the array represents a property of the surface 16. A location in the array corresponds to a spatial location on the sample's surface 16. Thus, the image defines a map corresponding to that property. Such a map shows the values of that property at different locations on the sample's surface 16 in much the same way a soil map shows different soil properties at different locations on the Earth's surface. Such a property will be referred to as a "mapped property."

In some cases, the mapped properties are physical properties. In other cases, the properties are geometrical properties. An example of a geometrical property is the height of the surface 16. Examples of physical properties include the surface's adhesion, its stiffness, and energy losses associated with contacting the surface 16.

A multichannel atomic force microscope 8 has the ability to map different properties at the same time. Each mapped property corresponds to a different "channel" of the microscope 8. An image can therefore be regarded as a multidimensional image array $M^{(k)}$, where the channel index, k, is an integer in the interval [1,K], where K is the number of channels.

When used in a sub-resonance tapping mode, a multichannel atomic force microscope 8 can map the following properties: height, adhesion, deformation, stiffness, viscoelastic losses, feedback error. This results in six channels, each of which corresponds to one of six mapped properties. When used in ringing mode, the atomic force microscope 8 can map, as an example, one or more of the following additional properties in addition to the previous six properties: restored adhesion, adhesion height, disconnection height, pull-off neck height, disconnection distance, disconnection energy loss, dynamic creep phase shift, and zero-force height. This results in a total of fourteen channels in this example, each of which corresponds to one of fourteen mapped properties.

The scanner 10 defines discrete pixels on the reference plane. At each pixel, the microscope's probe 14 makes a measurement. For convenience, the pixels on the plane can be defined by Cartesian coordinates $(x_i, y_j)$. The value of the $k^{th}$ channel measured at that pixel is $z_{i,j}^{(k)}$. With this in mind, an image array that represents a map or image of the $k^{th}$ channel can be formally represented as:

$$M^{(k)} = \{x_i, y_j, z_{i,j}^{(k)}\} \quad (1)$$

where "i" and "j" are integers in the intervals [1, Ni] and [1, Nj] respectively and where Ni and Nj are the numbers of pixels available for recording an image in the x and y directions respectively. The values of Ni and Nj can be different. However, the methods described herein do not depend significantly on such a difference. Hence, for purposes of discussion, Ni=Nj=N.

The number of elements in a sample's image array would be the product of the number of channels and the number of pixels. For a relatively homogeneous surface 16, it is only necessary to scan one region of the surface 16. However, for a more heterogenous surface 16, it is preferable to scan more than one region on the surface 16. By way of analogy, if one wishes to inspect the surface of the water in a harbor, it is most likely only necessary to scan one region because other regions would likely be similar anyway. On the other hand, if one wishes to inspect the surface of the city that the harbor serves, it would be prudent to scan multiple regions.

With this in mind, the array acquires another index to identify the particular region that is being scanned. This increases the array's dimensionality. A formal representation of the image array is thus:

$$M^{(k,s)} = \{x_i^{(s)}, y_j^{(s)}, z_{i,j}^{(k,s)}\} \quad (2)$$

where the scanned-region index s is an integer in the interval [1, S] that identifies a particular scanned region within a sample. Note that this causes the number of elements in the image array for a particular sample to grow by a factor equal to the number of scanned regions.

Preferably, the number of such scanned regions is large enough to be represent the sample as a whole. One way to converge on an appropriate number of scanned regions is to compare the distribution of deviations between two such scanned regions. If incrementing the number of scanned regions does not change this in a statistically significant way, then the number of scanned regions is likely to be adequate to represent the surface as a whole. Another way is to divide what is considered to be a reasonable testing time by the amount of time required to scan each scanned region and to use that quotient as the number of areas.

In some cases, it is useful to split each of the scanned regions into partitions. For the case in which there are P such partitions in each scanned region, the array can be defined as:

$$M^{(k;s;p)} = \{x_i^{(s;p)}, y_j^{(s;p)}, z_{i,j}^{(k;s;p)}\} \quad (2a)$$

where the partition-index p is an integer in the interval [1,P]. In the case of a square scanned area, it is convenient to divide the square into four square partitions, thus setting P to be equal to four.

The ability to divide a scanned region into partitions provides a useful way to exclude image artifacts. This is particularly important for inspection of biological cells 90. This is because the process of preparing cells 90 for inspection can easily introduce artifacts. These artifacts should be excluded from any analysis. This makes it possible to compare one partition against the others to identify which, if any, deviate significantly enough to be excluded.

On the other hand, the addition of a new index further increases the dimensionality of the array.

To identify a class to which a sample belongs based on the image arrays $M^{(k,s)}$ acquired by the atomic force microscope 8, the machine-learning module 84 relies in part on building a suitable database 86 that includes images of surfaces that are known a priori to belong to particular classes $C^{(l)}$. Such a database 86 can be formally represented by:

$$D_n^{(l;k;s;p)} = \{M_n^{(k;s;p)}, C^{(l)}\} \quad (2b)$$

where k is a channel index that represents a property or channel, s is a scanned-region index that identifies a particular scanned region, p is a partition index that represents a particular partition of the $s^{th}$ scanned region, n is a sample index that identifies a particular sample, and l is a class index that identifies a particular class from a set of L classes. The overall size of the array is thus the product of the number of classes, the number of samples, the number of scanned regions, the number of partitions per scanned region, and the number of channels.

FIG. 3 shows a diagnostic method 10 that features using an atomic force microscope 8 operated using sub-resonance tapping and the machine-learning module 84 to inspect surfaces of biological cells 90 that have been recovered from urine 88 in an effort to classify patients into one of two classes: cancer-afflicted and cancer-free. Since there are two classes, L=2.

A preferred practice includes collecting the cells 90 using centrifugation, gravitational precipitation, or filtration followed by fixing, and freeze drying or subcritical drying the cells 90.

In the example shown, the atomic force microscope 8 was operated using both sub-resonant tapping modes, such as PeakForce QMN as implemented by Bruker, Inc., and ringing modes. Both modes allow to record height and adhesion channels. Ringing mode is, however, a substantially faster mode of image collection. As noted above, these modes allow many channels to record simultaneously. However, only two channels are used in the experiment described herein.

Figure 4:
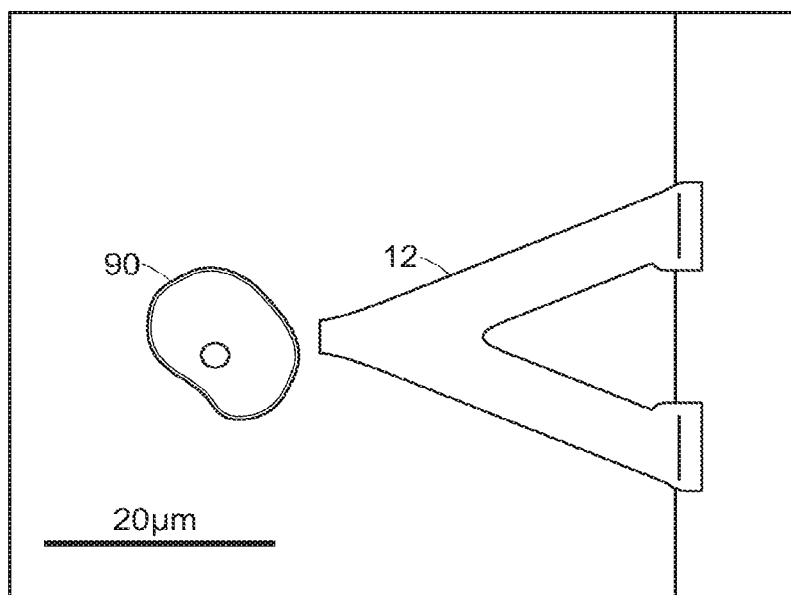
FIG. 4 shows the view through an optical microscope built into the atomic force microscope shown in FIG. 1.

FIG. 4 shows the atomic force microscope's cantilever 12 together with a cell 90 obtained from a patient and prepared as described above. The view is taken through an optical microscope that is coupled to the atomic force microscope 8.

Figure 5:
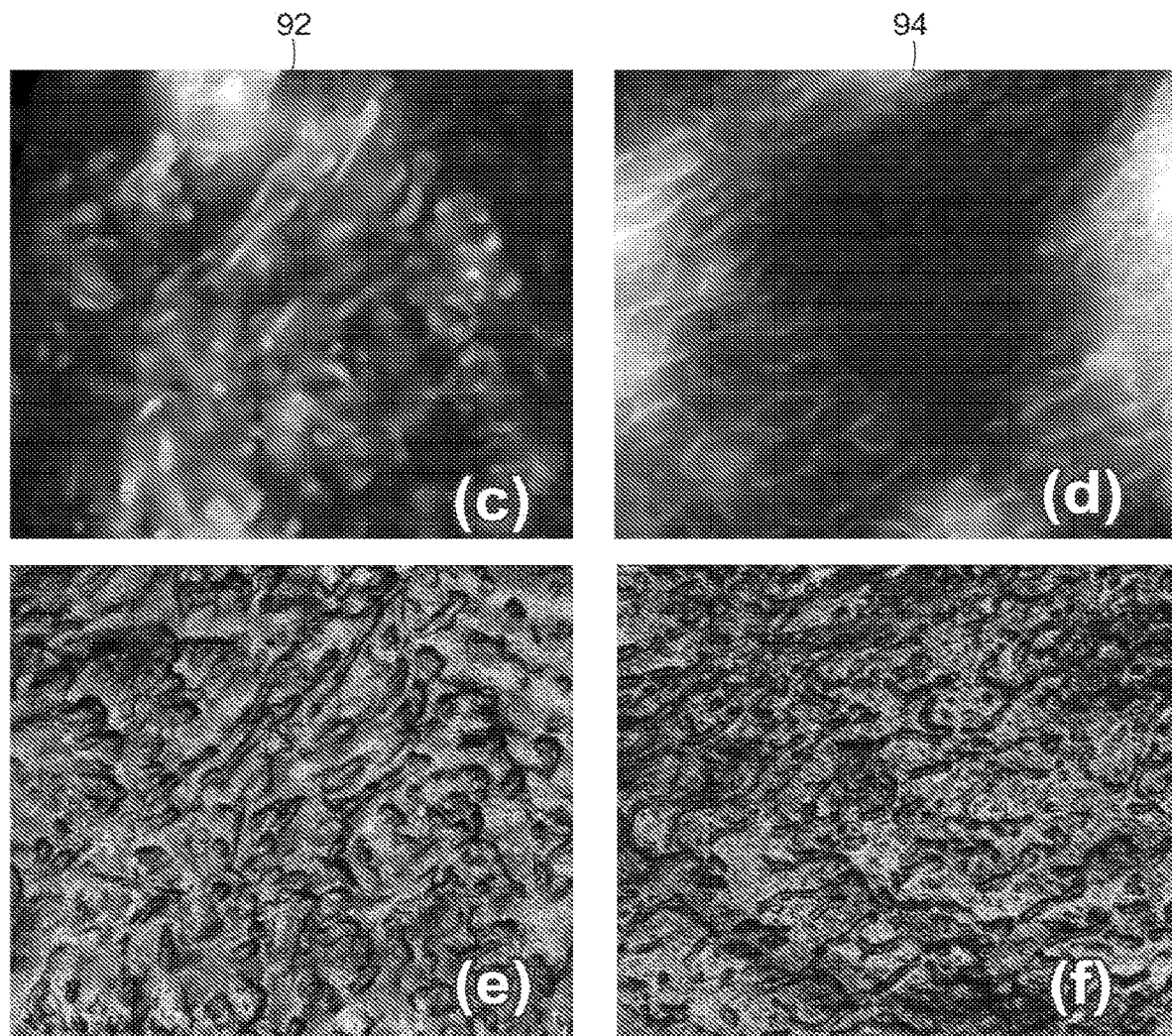
FIG. 5 shows maps of bladder cells acquired by the atomic force microscope of FIG. 1.

FIG. 5 show first and second map pairs 92, 94. The first map pair 92 shows maps of a cell 90 from a cancer-free patient. The second map pair 94 shows maps of a cell 90 from a cancer-afflicted patient. The maps shown are those of a square scanned area that is ten micrometers on a side with a resolution of 512 pixels in both dimensions. The scan speed was 0.1 Hz when scanning in a sub-resonant tapping mode, such as PeakForce QMN mode, and 0.4 Hz when scanning in ringing mode. The peak force during scanning is five nano-newtons.

Referring now to FIG. 6, the machine-learning module 84 trains a candidate classifier 100 based on the database 86. A particular machine learning method can be chosen from the family of machine learning methods, for example, learning trees, neural networks, or combinations thereof.

Figure 7:
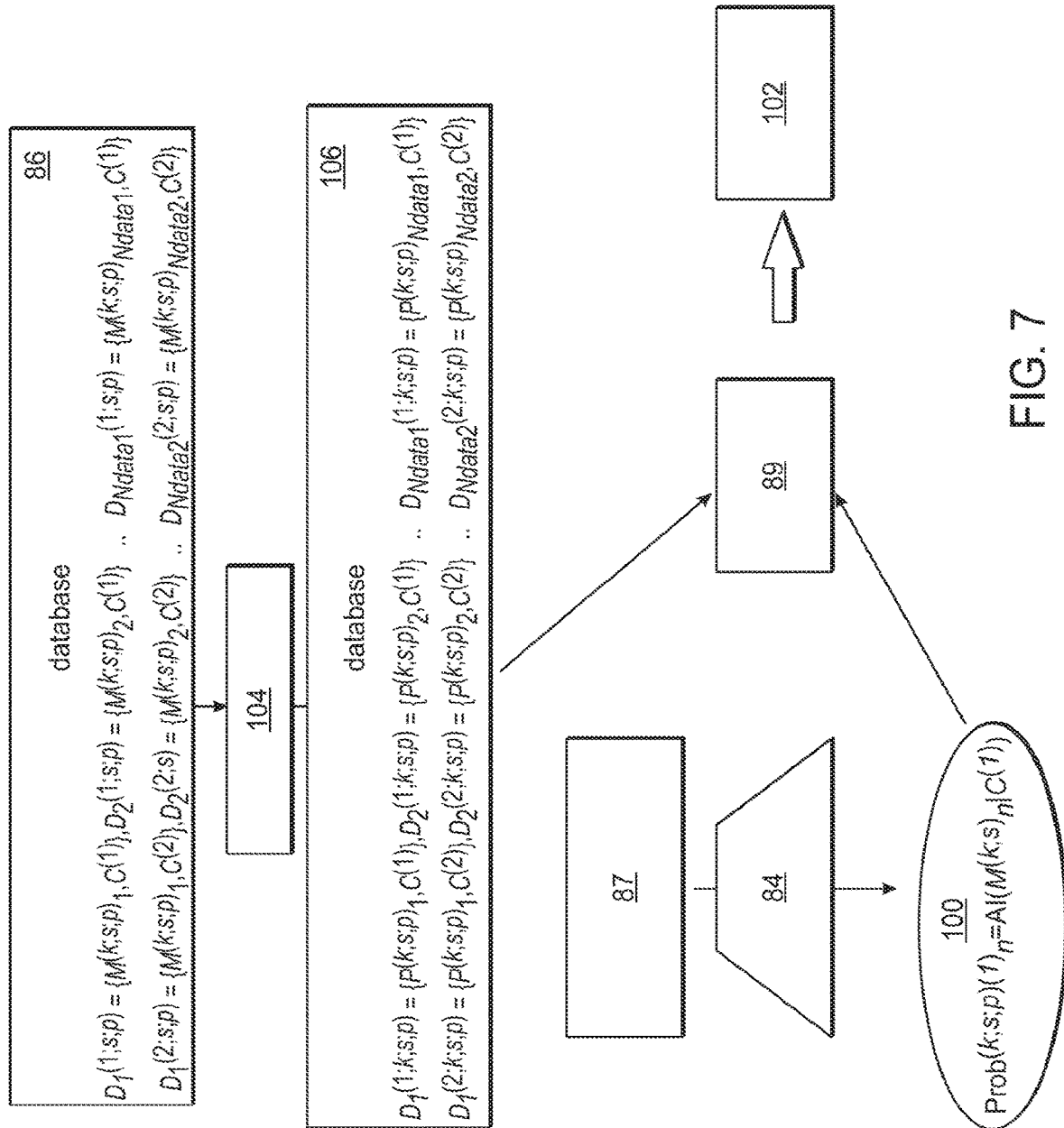
FIG. 7 shows details of condensing the initial large database into a condensed database of smaller dimension and shows the details of interactions between the condensed database and the machine-learning module in the processing system of FIG. 2.

The methods shown in FIG. 6 and FIG. 7 begin by splitting the database 86 into training data 87 and testing data 89. This raises the question of how much of the data in the database 86 should go into the training data 87 and how much should go into the testing data 89.

In some embodiments, 50% of the database 86 goes into the training data 87 and the remaining 50% goes into the testing data 89. In other embodiments, 60% of the database 86 goes into the training data 87 and the remaining 40% goes into the testing data 89. In yet other embodiments, 70% of the database 86 goes into the training data 87 and the remaining 30% goes into the testing data 89. In still other embodiments, 80% of the database 86 goes into the training data 87 and the remaining 20% goes into the testing data 89. The candidate classifier 100 should ultimately be independent of the ratio used in the split.

In the example illustrated in FIG. 3, ten bladder cells 90 were gathered for each patient. The presence of cancer was identified using standard clinical methods including invasive biopsies and histopathology. These methods are reliable enough for the two classes to be regarded as well defined. As a result, the database 86 shown in FIG. 6 can be represented as:

$$D_1^{(1;k;s;p)} = \{M^{(k;s;p)}_1, C^{(1)}\}, D_2^{(1;k;s;p)} = \{M^{(k;s;p)}_2, C^{(1)}\} \ldots D_{Ndata1}^{(1;k;s;p)} = \{M^{(k;s;p)}_{Ndata1}, C^{(1)}\}$$
$$D_1^{(2;k;s;p)} = \{M^{(k;s;p)}_1, C^{(2)}\}, D_2^{(2;k;s;p)} = \{M^{(k;s;p)}_2, C^{(2)}\} \ldots D_{Ndata2}^{(2;k;s;p)} = \{M^{(k;s;p)}_{Ndata2}, C^{(2)}\}, \quad (3)$$

where $N_{data1}$ is the number of patients that are in a first class, $N_{data2}$ is the number of patients that are in a second class, and s, which is a whole number between one and ten inclusive, identifies the particular one of ten cells collected from a single patient. It is not necessary that $N_{data1}$ and $N_{data2}$ be equal.

When splitting the database 86 between the training data 87 and the testing data 89, it is important to avoid having image arrays for different scanned areas from the same sample $\{M^{(k;1;p)}, M^{(k;2;p)} \ldots M^{(k;S;p)}\}$ be divided between training and testing data 87, 89. Violation of this rule would result in training and testing on the same sample. This would artificially pump up the classifier's effectiveness in a way that may not be reproducible when applying the classifier 100 to independent new samples.

The machine-learning module 84 uses the training data 87 to build the candidate classifier 100. Depending on the type of classifier 100, the training data 87 can be a learning tree, a decision tree, a bootstrap of trees, a neural network, or combinations thereof. The classifier 100, which is represented below as "AI," outputs a probability that a particular sample n belongs to a particular class l:

$$\text{Prob}_n^{(k;s;p)(l)} = AI(M_n^{(k;s;p)} | C^{(l)}) \quad (3a)$$

where $\text{Prob}_n^{(k;s;p)(l)}$ is the probability that the image or channel defined by $M_n^{(k;s;p)}$ belongs to class $C^{(l)}$.

After having been built, a verification module 102 uses the testing data 89 to verify that the candidate classifier 100 is, in fact, sufficiently effective. In the embodiment described herein, the verification module 102 evaluates effectiveness based at least in part on a receiver operating characteristic and on a confusion matrix. The robustness of the candidate classifier 100 was verified by repeating the random splitting of the database 86 to thereby generate different testing data 89 and training data 87 and then carrying out the classification procedure to see if this made in any difference.

If the candidate classifier 100 turns out to be insufficiently effective, the machine-learning module 84 changes the parameters of the training process and generates a new candidate classifier 100. This cycle continues until the machine-learning module 84 eventually provides a candidate classifier 100 that attains a desired threshold of effectiveness.

The process of building a suitable classifier 100 is hindered to some extent by the computational load that arises when there is more than one probability value associated with a sample n. In fact, as a result of the multidimensional nature of the image array, for any one sample, there would be K·S·P probabilities, $\text{Prob}_n^{(k;s;p)(l)}$ to process. The required computational load would be impractically high for such a large database.

Another bottleneck of dealing with such large arrays of data is the large number of samples used to provide a reasonable training of the classifiers. When building decision trees, a rule of thumb requires the number of samples to be at least six times larger than the dimension of the database. Because atomic force microscopy is a relatively slow technique, it would be impractical to obtain enough samples to build any reasonable classifier.

A condenser 104, as shown in FIG. 7, addresses the foregoing difficulty. The condenser 104 condenses information provided by a particular channel into a space of surface parameters that embodies information about that channel. The condenser 104 receives the database 86 and generates a condensed database 106. In effect, this amounts to projecting a multidimensional matrix that is in a fairly high-dimensional space into a matrix of much less dimensionality.

The condenser 104 carries out any of a variety of database-reduction procedures. Among these are procedures that combine one or more of the database-reduction procedures described herein. These have in common deriving, from a set of data, a surface parameter that embodies at least some of the information embodied in that set.

In some practices, the condenser 104 carries out a first database-reduction procedure. This first database-reduction procedure relies on the observation that each image is ultimately an array that can be combined with other such arrays in a way that yields an object that preserves enough aspects of the information from the arrays that went into it so as to be useful in classifying a sample. For example, tensor addition "⊕" can be used to combine a set of images $M_n^{(k;s;p)}$ along a slice corresponding to one of its indices.

In one specific implementation, the slice corresponds to the index k. In that case, the tensor sum of the images is given by:

$$M_n^{(1;s;p)} \oplus M_n^{(2;s;p)} \oplus M_n^{(3;s;p)} \oplus \ldots M_n^{(K;s;p)}$$

Thus, each element of the condensed database 106 to be used for machine learning becomes the following:

$$D_n^{(1;s;p)} = \{M_n^{(1;s;p)} \oplus M_n^{(2;s;p)} \oplus M_n^{(3;s;p)} \oplus \ldots M_n^{(K;s;p)}\} \quad (3\text{-}1)$$

This particular example decreases the dimensionality of the database 86 by a factor of K. Therefore, the classifier 100 defines the probability as follows:

$$\text{Prob}_n^{(s;p)(1)} = AI(M_n^{(1;s;p)} \oplus M_n^{(2;s;p)} \oplus M_n^{(3;s;p)} \oplus \ldots M_n^{(K;s;p)} | C^{(1)})$$

It is also possible to carry out a similar procedure for the remaining indices. Ultimately, $$\text{Prob}_n^{(l)} = AI(\oplus \oplus \oplus M_n^{(k;s;p)} | C^{(l)})$$

where "⊕⊕⊕" represents a tensor summation over the indices k,s,p.

In other practices, the condenser 104 instead carries out a second database-reduction procedure. This second database-reduction procedure relies on geometrical or algebraic averaging on each of the indexes k,s,p separately or their combination. Examples of particular ways to carry out the second procedure include the following averaging procedures over all indices k,s,p:

$$\text{Prob}_n^{(l)} = \frac{1}{K \times S \times P} \sum_{k,s,p} \text{Prob}_n^{(k;s;p)(l)}, \quad (3\text{-}2)$$

$$\text{Prob}_n^{(l)} = \frac{1}{\sqrt[3]{K \times S \times P}} \prod_{k,s,p} \text{Prob}_n^{(k;s;p)(l)}, \quad (3\text{-}3)$$

$$\text{Prob}_n^{(l)} = \frac{1}{K \times S \times P} \sum_{k,s,p} (1 - \text{Prob}_n^{(k;s;p)(l)}), \quad (3\text{-}4)$$

$$\text{Prob}_n^{(l)} = \frac{1}{\sqrt[3]{K \times S \times P}} \prod_{k,s,p} (1 - \text{Prob}_n^{(k;s;p)(l)}), \quad (3\text{-}5)$$

In yet other practices, the condenser 104 instead carries out a third database-reduction procedure. This third database-reduction procedure relies on assigning the highest or lowest probability of the entire series to a particular index. For example, considering scanned-region index s, one can use one of the following relationships:

$$\text{Prob}_n^{(k;p)(l)} = \max_s \{\text{Prob}_n^{(k;s;p)(l)}\}, \quad (3\text{-}6)$$

$$\text{Prob}_n^{(k;p)(l)} = \min_s \{\text{Prob}_n^{(k;s;p)(l)}\}. \quad (3\text{-}7)$$

Ultimately, if all indexes are reduced this way $$\text{Prob}_n^{(l)} = \max_{k,s,p} \{\text{Prob}_n^{(k;s;p)(l)}\} \quad (3\text{-}8)$$

or $$\text{Prob}_n^{(l)} = \min_{k,s,p} \{\text{Prob}_n^{(k;s;p)(l)}\}. \quad (3\text{-}9)$$

In some practices, the condenser 104 reduces the dimensionality of the database $D_n^{(l;s)}$ by passing each image through a surface-parameter extractor $A_m$ to obtain a surface-parameter set, $P_{nm}^{(k,s)}$. This can be represented formally by:

$$P_{nm}^{(k,s)} = A_m\{M_n^{(k;s;p)}\} \tag{4}$$

where the surface-parameter index m is an integer in [1,M], the channel index k identifies whether the map represents height, adhesion, stiffness, or some other physical or geometric parameter, the sample index n identifies the sample, the scanned-region index s identifies the particular scanned region with in a sample, and the partition index p identifies the particular partition within a scanned region. This procedure provides a compact way to represent a multidimensional tensor $M_n^{(k;s;p)}$ as a surface-parameter vector $P_{nm}^{(k,s,p)}$.

The surface-parameter vector includes enough residual information concerning the channel from which it was derived to be usable as a basis for classification. However, it is much smaller than the image provided by the channel. As such, a classification procedure that relies on the surface-parameter vector sustains a much lower computational load but without a corresponding loss of accuracy.

A variety of surface parameters can be extracted from a channel. These include roughness average, root mean square, surface skew, surface kurtosis, peak-peak, ten-point height, maximum valley depth, maximum peak height, mean value, mean summit curvature, texture index, root mean square gradient, area root mean square slope, surface area ratio, projected area, surface area, surface bearing index, core fluid retention index, valley fluid retention index, reduced summit height, core roughness depth, reduced valley depth, I-h % height intervals of bearing curve, density of summits, texture direction, texture direction index, dominant radial wave length, radial wave index, mean half wavelength, fractal dimension, correlation length at 20%, correlation length at 37%, texture aspect ratio at 20%, and texture aspect ratio at 37%.

The list of surface parameters may be further extended by introducing the algorithms or mathematical formulas. For example, one can normalize the surface parameters to a surface area of the images, which can be different for different cells, by for example, dividing each parameter by a function of the surface area.

The example described herein relies on three surface parameters: valley fluid retention index ("Svi"), the Surfaces Area Ratio ("Sdr"), and the Surface Area, ("S3A").

The valley fluid retention index is a surface parameter that indicates the existence of large voids in a valley zone. It is defined by:

$$Svi = \frac{V(h_{0.80})}{(M-1)(N-1)\delta x \delta y} \Big/ Sq, \tag{5}$$

where N is the number or pixels in the x direction, M is the numbers of pixels in the y direction, $V(h_x)$, is a void area over the bearing area ratio curve and under the horizontal line $h_x$, and $S_q$ is the Root Mean Square (RMS), which is defined by the following expression:

$$Sq = \sqrt{\frac{1}{MN} \sum_{k=0}^{N-1} \sum_{l=0}^{M-1} [h(x_k, y_l)]^2} \tag{6}$$

The surfaces area ratio ("Sdr") is a surface parameter that expresses the increment of the interfacial surface area relative to the area of the projected x, y plane. This surface parameter is defined by:

$$S_{sd} = \frac{\left(\sum_{k=0}^{M-2}\sum_{l=0}^{N-2} A_{kl}\right) - (M-1)(N-1)\delta x \delta y}{(M-1)(N-1)\delta x \delta y} 100\%, \tag{7}$$

where N is the number of pixels in the x direction and M is the numbers of pixels in the y direction.

The Surface Area, ("S3A") is defined by:

$$S3A = \left(\sum_{k=0}^{M-2}\sum_{l=0}^{N-2} A_{kl}\right) - (M-1)(N-1)\delta x \delta y. \tag{8}$$

To calculate each of the above-mentioned three surface parameters from images provided by the atomic force microscope 8, each image of a cell was first split into four partitions, which in this case were quadrants of a square having five-micrometer sides. Thus, each cell yielded four sets of surface parameters, one for each quadrant.

The presence of artifacts in a cell can be addressed in any one of three different ways.

A first way is to have an operator inspect the cells for artifacts and exclude, from further processing, any cell that had one or more such artifacts. This requires human intervention to identify artifacts.

A second way is to provide an artifact-recognition module that is able to recognize an artifact and automatically exclude the cell that contains that artifact. This renders the procedure more operator-independent.

A third way is to use the median value of the parameters for each cell instead of the mean values. The results described herein were virtually unchanged when the median value was used instead of the mean value.

Using the same example of just two classes, the condensed database 106 will look as follows $$D_1^{(1;k;s;p)} = \{P^{(k;s;p)}{}_1, C^{(1)}\}, D_2^{(1;k;s;p)} = \{P^{(k;s;p)}{}_2,$$
$$C^{(1)}\} \ldots D_{Ndata1}^{(1;k;s;p)} = \{P^{(k;s;p)}{}_{Ndata1}, C^{(1)}\}$$
$$D_1^{(2;k;s;p)} = \{P^{(k;s;p)}{}_1, C^{(2)}\}, D_2^{(2;k;s;p)} = \{P^{(k;s;p)}{}_2,$$
$$C^{(2)}\} \ldots D_{Ndata2}^{(2;k;s;p)} = \{P^{(k;s;p)}{}_{Ndata2}, C^{(2)}\}, \tag{3}$$

In other embodiments, one can assign additional parameters to help differentiate between different classes even though these parameters are not directly related to the atomic force microscope's images.

For example, when attempting to detect bladder cancer, it is quite possible that one or more samples of urine 88 will not have any cells 90. A convenient way take into account such a result is to add a new "no cell" parameter that is either true or false. To avoid having to alter the data structure to accommodate such a parameter, a sample with a "no cell" set to "true" receives artificial values for surface parameters that are selected to avoid distorting the statistical results.

As another example, there are other factors that are not related to surface parameters but are nevertheless pertinent to classification. These include characteristics of patients, like age, smoking, and family history, all of which may be relevant to the probability of that patient having bladder cancer. These parameters can be included in a manner similar to the "no cell" parameter so as to avoid having to modify the data structure.

There exist yet other ways to use surface parameters to reduce the size of the database 86.

One such procedure is that of excluding surface parameters that are sufficiently correlated with each other. Some surface parameters depend strongly on various other surface parameters. Hence, little additional information is provided by including surface parameters that are correlated with each other. These redundant surface parameters can be removed with little penalty.

Figure 8:
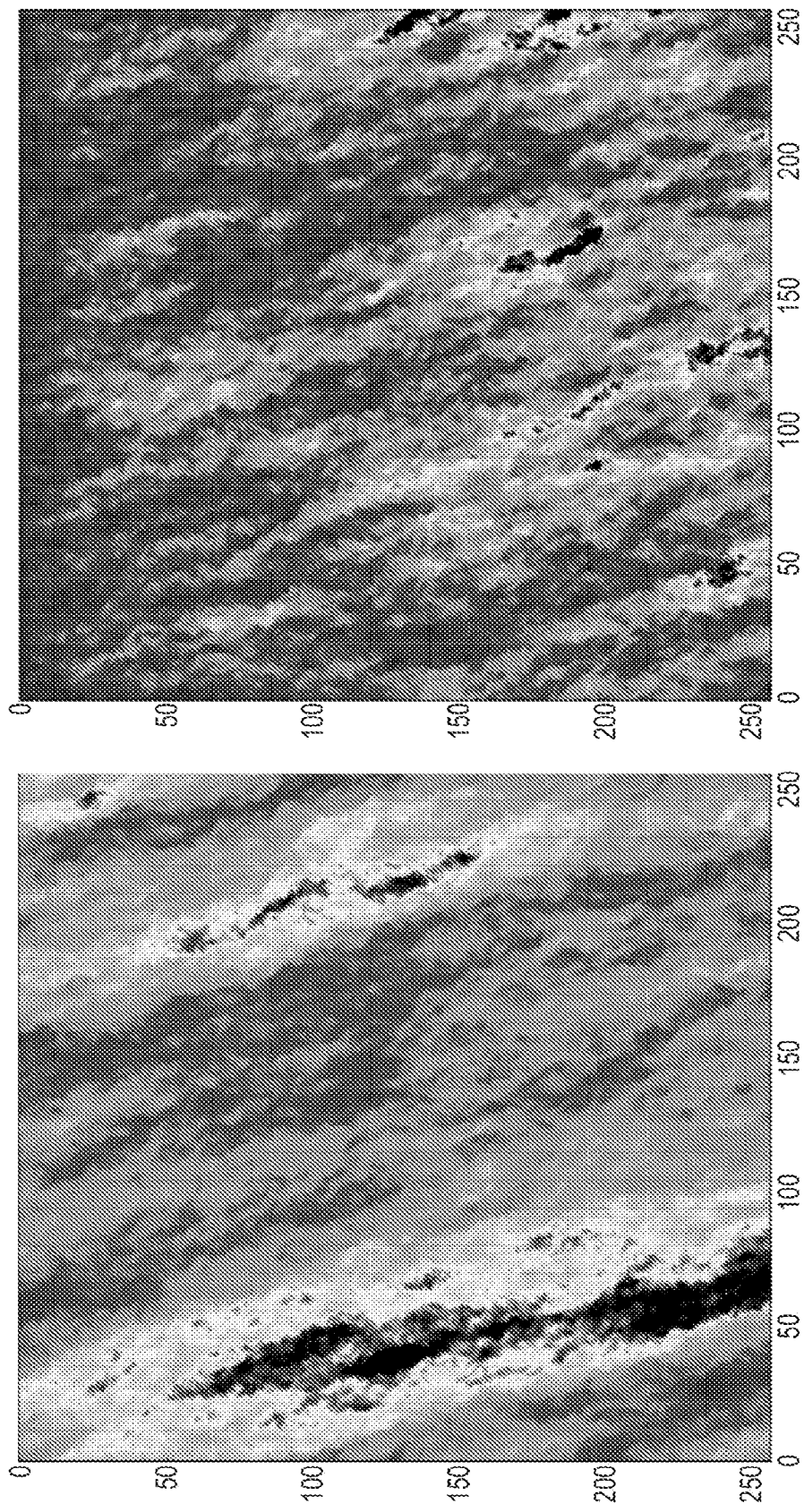
FIG. 8 shows examples of simulated surfaces used in connection with evaluating correlation between different surface parameters.

One way to find the correlation matrix between surface parameters is to generate simulated surfaces, examples of which are shown in FIG. 8. Various sample surfaces imaged with an atomic force microscope 8 can also be used to identify correlation between different surface parameters.

The machine-learning module 84 is agnostic to the nature of its inputs. Thus, although it is shown as operating on an image array, it is perfectly capable of operating on the surface-parameter vector instead. The same machine-learning module 84 is therefore usable to determine the probability that a particular surface-parameter vector belongs to a particular class, i.e., to evaluate $\text{Prob}_n^{(k;s;p)(l)} = AI(P_n^{(k;s;p)}|C^{(l)})$.

Therefore, after having reduced the multidimensional image array $M_n^{(k;s;p)}$ into a surface-parameter vector $P_{nm}^{(k;s;p)}$, it becomes possible to substitute the surface-parameter vector $P_{nm}^{(k;s;p)}$ for the multidimensional image array $M_n^{(k;s;p)}$ and to then have the machine-learning module 84 learn what surface parameters are important for classification and how to use them to classify cells.

Because certain surface parameters are correlated with each other, it is possible to further reduce the dimensionality. This can be carried out without tensor summation. Instead, such reduction is carried out by direct manipulation of the same parameters from different images.

In addition to the methods that rely on the database-reduction procedures identified above as (3-1) to (3-9), it is also possible to use a classifier 100 that combines different surface parameters of the same kind from the same sample. Formally, this type of classifier 100 can be represented formally as:

$$\text{Prob}_n^{(l)} = AI(P_n|C^{(l)}) \quad (10)$$

where $P_n = F(P_{nm}^{(k;s;p)})$ and where $F(P_{nm}^{(k;s;p)})$ is a combination of different surface parameters identified by the surface-parameter index m and belonging to the sample identified by the sample index n.

A related classifier 100 is one that combines different surface parameters of the same kind m of the same sample n from the images of the same properties. Such a classifier 100 can be represented formally as:

$$\text{Prob}_n^{(k)(l)} = AI(P_{nm}^{(k)}|C^{(l)}) \quad (11)$$

where $P_{nm}^{(k)} = F(P_{nm}^{(k;s;p)})$ and $F(P_{nm}^{(k;s;p)})$ is a combination of different surface parameters identified by the same surface-parameter index m of the sample identified by the sample index n and from the channel identified by the channel index k.

Yet another classifier 100 is one that does not combine all parameters but instead combines surface parameters by only one index. One such classifier 100 assigns one surface parameter to an entire series of partitions p within the same image. Such a classifier 100 is formally represented as:

$$\text{Prob}_n^{(k;s)(l)} = AI(P_{nm}^{(k;s;p)}|C^{(l)}) \quad (12)$$

where $P_{nm}^{(k;s)} = F(P_{nm}^{(k;s;p)})$ and $F(P_{nm}^{(k;s;p)})$ is a combination of surface parameters, examples of which include a parameter associated with a statistical distribution of $P_{nm}^{(k;s;p)}$ over the partition index. Examples include the average:

$$P_{nm}^{(k;s)} = \frac{1}{N} \sum_{p=1}^{N} P_{nm}^{(k;s;p)} \quad (13)$$

and the median:

$$P_{nm}^{(k;s)} = \text{median}\{P_n^{(k;s;p)}\} \text{ for } p=1 \ldots N \quad (14)$$

When used in connection with detection bladder cancer imaging of multiple cells from each patient, the classifier 100 relies on either the average or the median. However, it is preferable for the classifier 100 to rely on the median rather than the average because the media is less sensitive to artifacts.

In the particular embodiment described herein, the machine-learning module 84 implements any of a variety of machine-learning methods. However, when confronted with multiple parameters, a machine-learning module 84 can easily become over-trained. It is thus useful to use three methods that are least prone to overtraining, namely the Random Forest method, the Extremely Randomized Forest method, and the method of Gradient Boosting Trees.

The Random Forest method and the Extremely Randomized Forest method are bootstrap unsupervised methods. The method of Gradient Boosting Trees is a supervised method of building trees. Variable ranking, classifier training, and validation were carried out using appropriate classifier functions from the SCIKIT-LEARN Python machine-learning package (version 0.17.1).

The Random Forest and Extremely Randomized Forest methods are based on growing many classification trees. Each classification tree predicts some classification. However, the votes of all trees define the final classification. The trees are grown on the training data 87. In a typical database 86, 70% of all data is in the training data 87 with the remainder being in the testing data 89. In the experiments described herein, the split between training data 87 and testing data 89 was random and repeated multiple times to confirm that the classifiers 100 were insensitive to the manner in which the database 86 was split.

Each branching node relies on a randomly chosen subset of the original surface parameters. In the methods described herein, the number of elements in the chosen subset of original surface parameters is the square root of the number of surface parameters originally provided.

The learning process then proceeds by identifying the best split of the tree branches given the randomly chosen subset of surface parameters. The machine-learning module 84 bases the split threshold is based on an estimate of the classification error. Each parameter is assigned to a parameter region with respect to the most commonly occurring class of the training data 87. In these practices, the machine-learning module 84 defines the classification error as a fraction of the training data 87 in that region that does not belong to the most common class:

$$E = 1 - \max_k(p_{mk}) \quad (15)$$

where $p_{mk}$ represents the proportion of training data 87 that is both in the $m^{th}$ region and that also belong to the $k^{th}$ class. However, for a practical use, equation (1) is not sufficiently sensitive to avoid overgrowing the tree. As a result, the machine-learning module 84 relies on two other measures: the Gini index and cross-entropy.

The Gini index, which is a measure of variance across all K classes, is defined as follows:

$$G = \sum_{k=1}^{K} p_{mk}(1 - p_{mk}). \quad (16)$$

The Gini index remains small when all values of $p_{mk}$ remain close to zero or unity. As a result, the Gini index measures an extent to which a particular node contains mostly samples from a single class. This is referred to as the extent of "node purity." Thus, to avoid overgrowing, each tree is grown only until the Gini-index results in complete separation of classes. This occurs when two descendant nodes yield a Gini-index that is less than that of the parent node. There is no pruning of the growing branches in these Random Forest methods.

The cross-entropy, which also provides a metric for node purity, is defined as:

$$D = -\sum_{k=1}^{K} p_{mk} \log(p_{mk}) \quad (17)$$

Like the Gini index, cross-entropy is small when all values of $p_{mk}$ are close to zero. This is indicative of a pure node.

The Gini index also provides a way to obtain an "importance coefficient" that is indicative of the importance of each surface parameter. One such measure comes from adding all values of the decrease of the Gini index at the tree nodes for each of the variables and averaging over all the trees.

Figure 9:
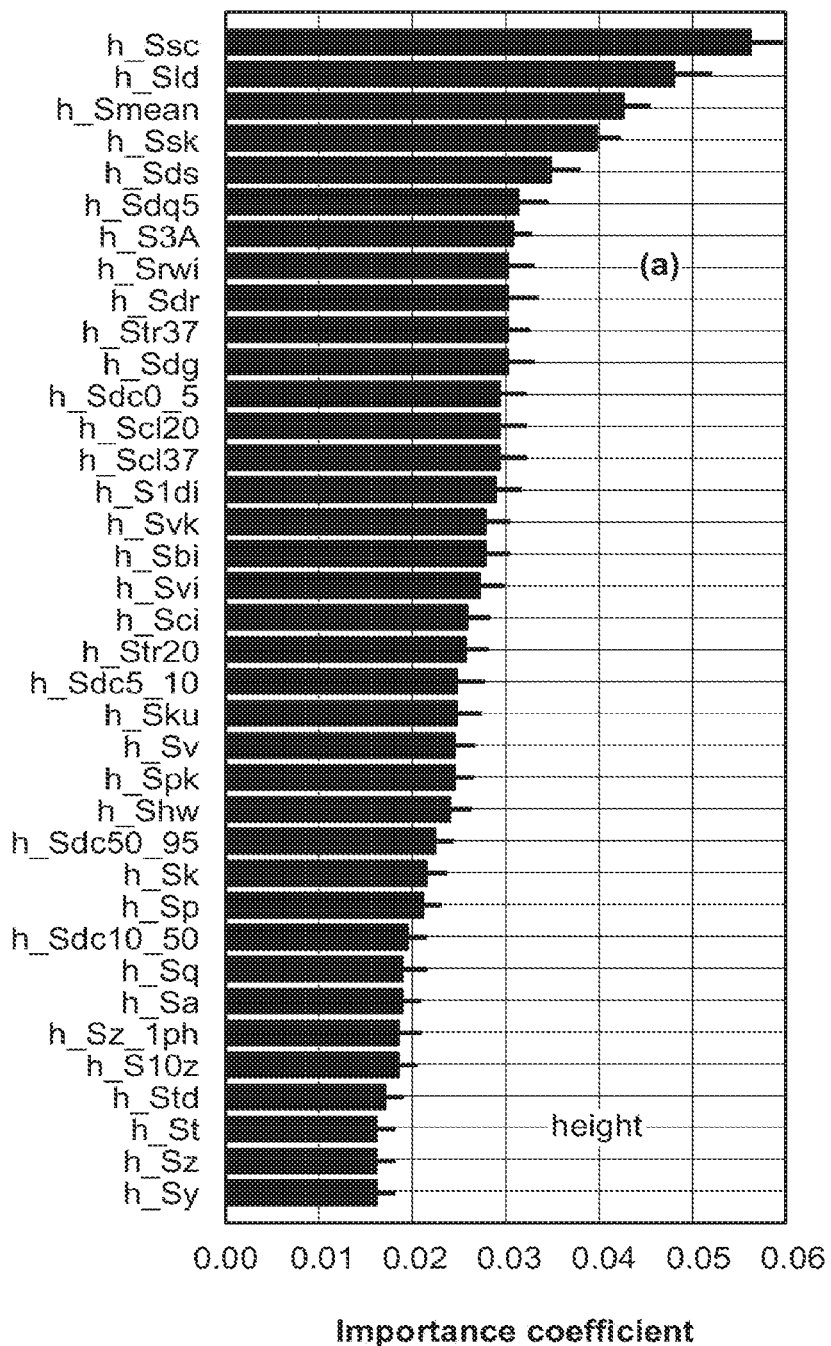
FIG. 9 shows a histogram plot of an importance coefficient for two surface parameters.
Figure 9:
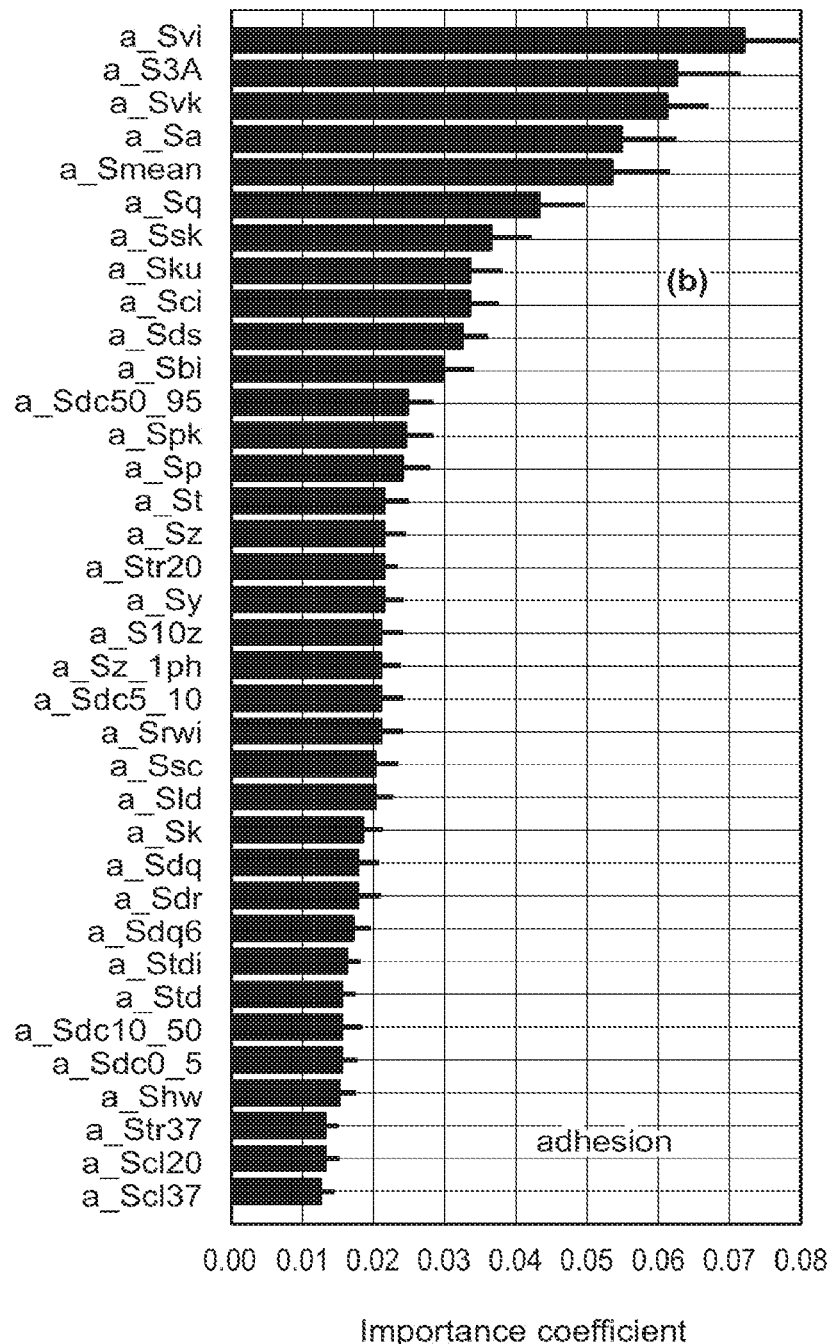
Figure 9:
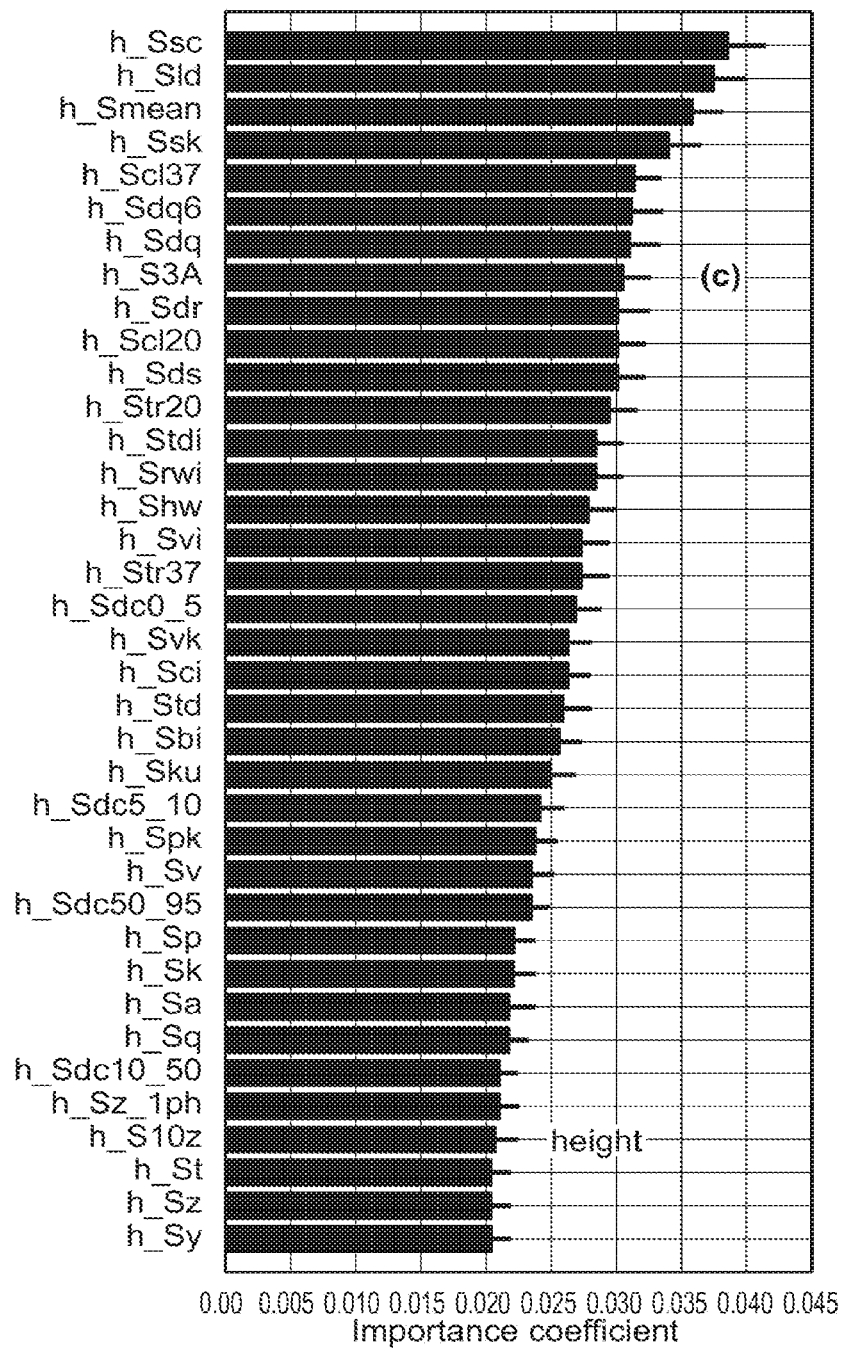
Figure 9:
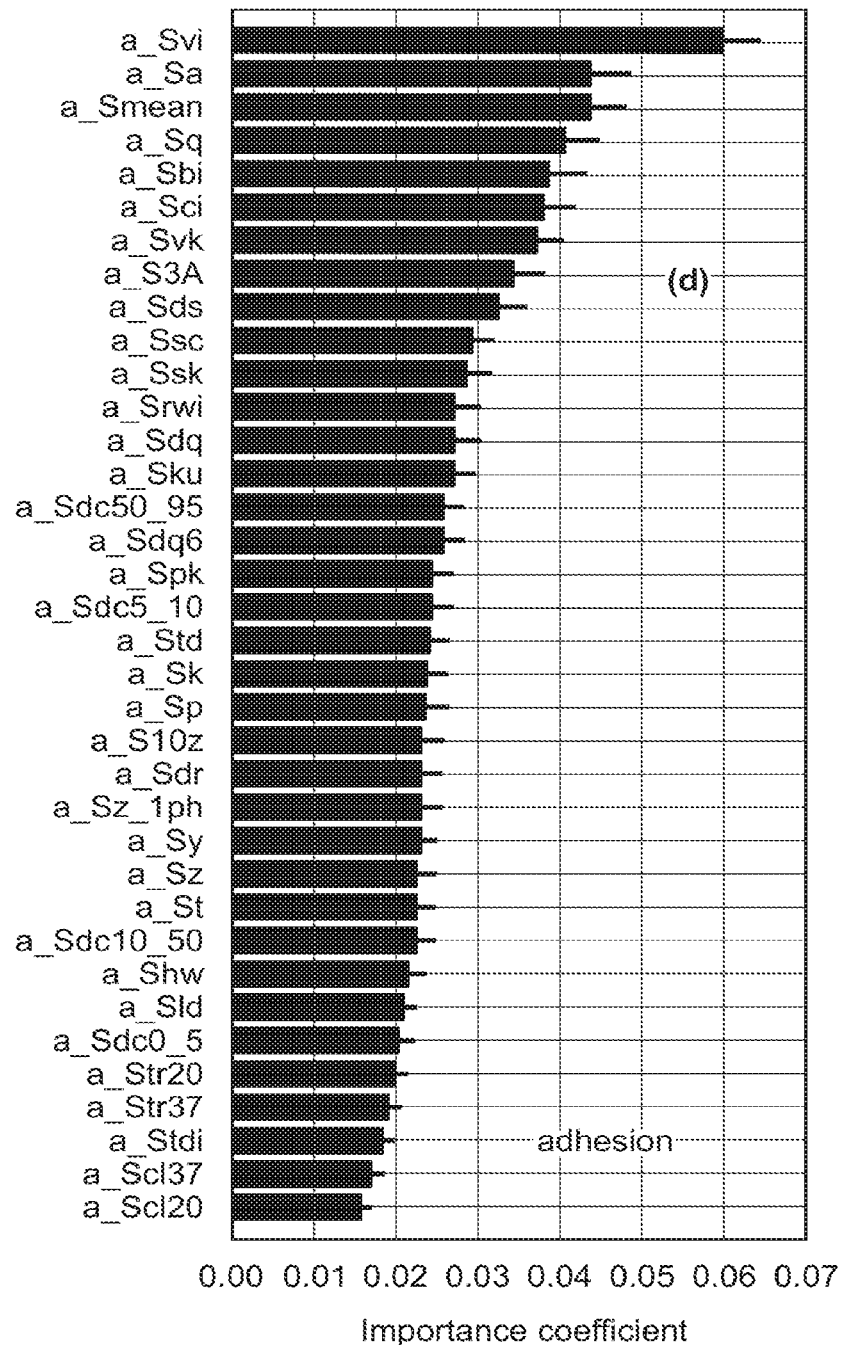
Figure 9:
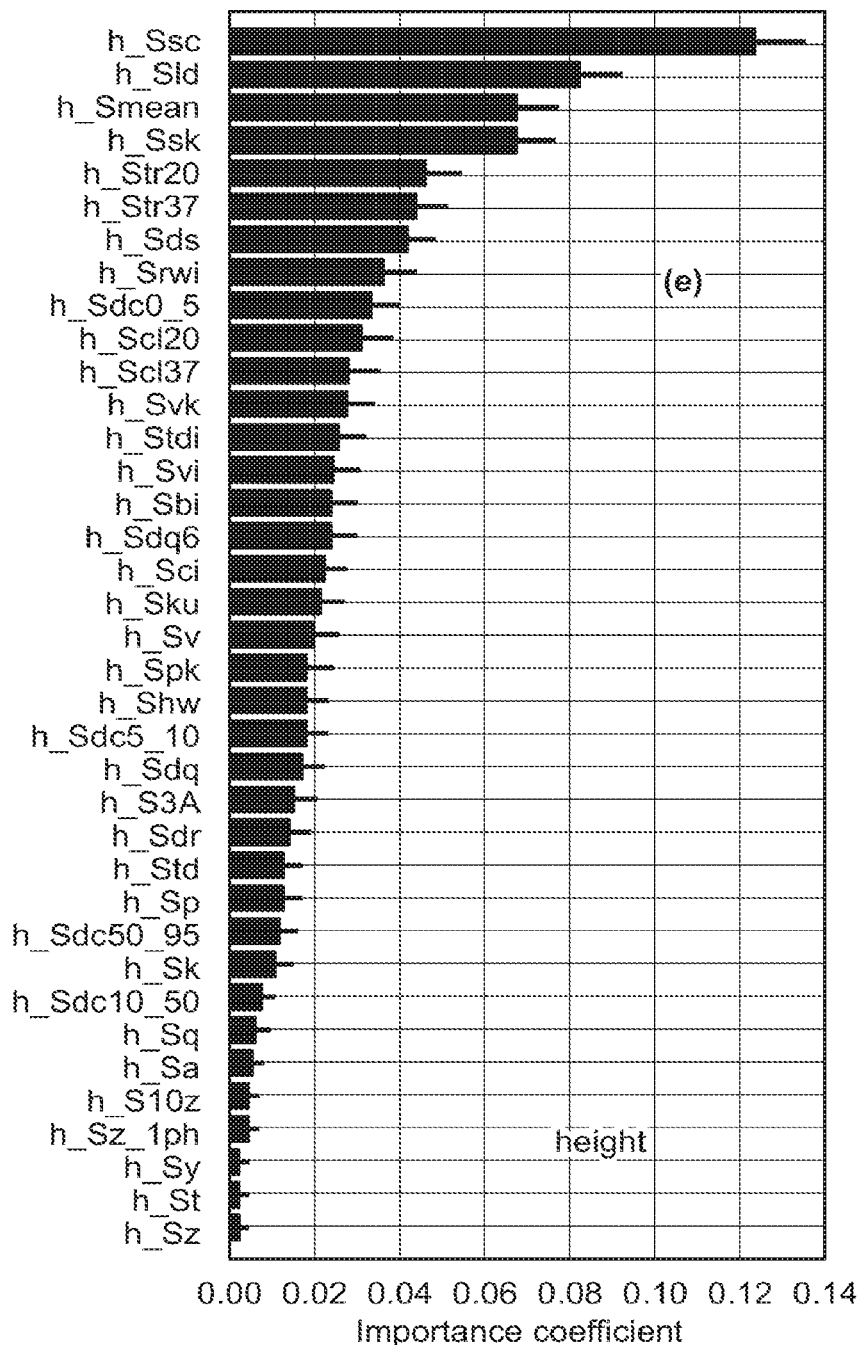
Figure 9:
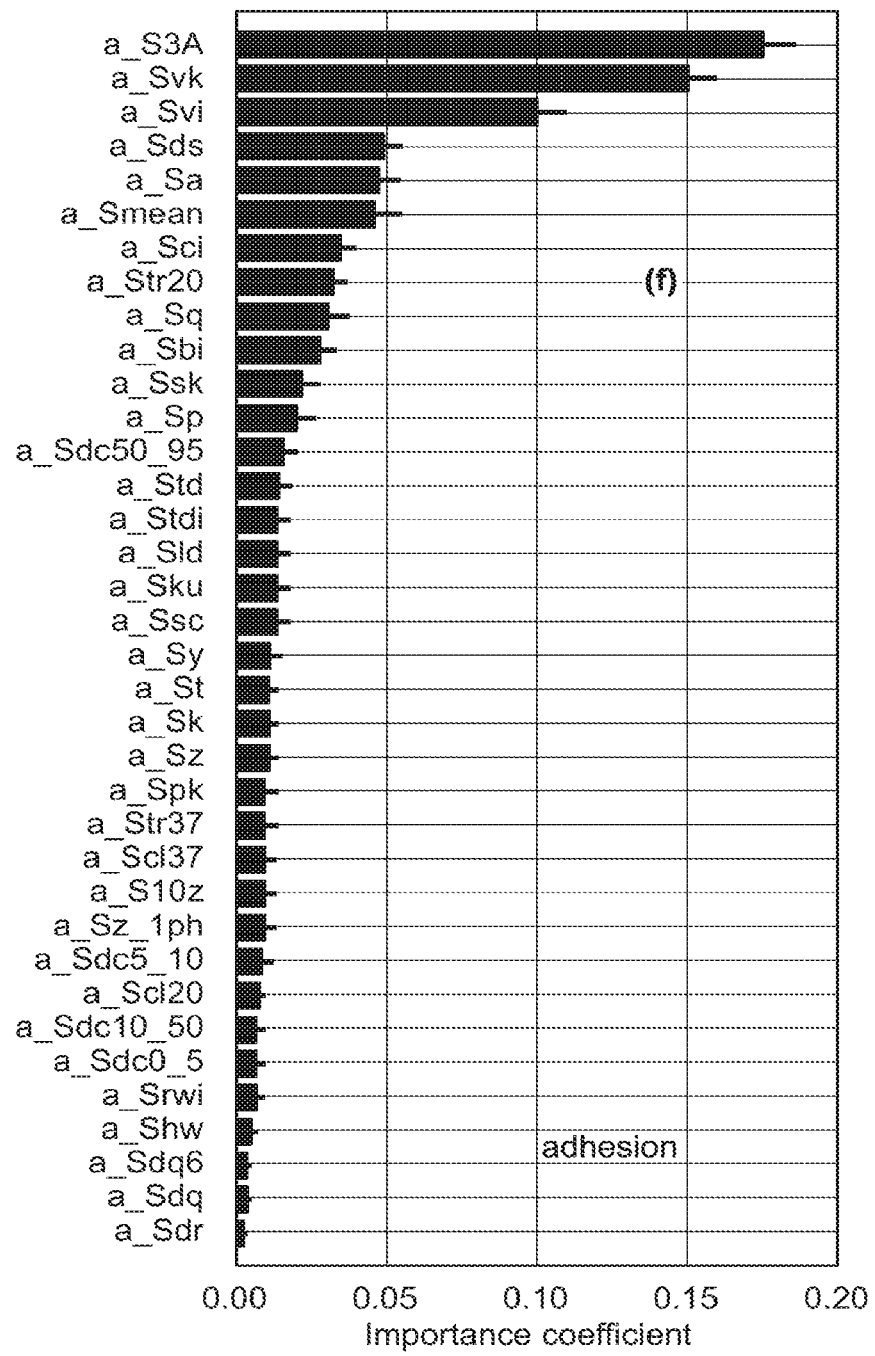

The histograms shown in FIG. 9 represent average values for importance coefficients with error bars to show the extent to which they deviate by one-standard-deviation from the mean. These importance coefficients correspond to the various surface parameters that can be derived from a particular channel. Thus, the histograms in the first row represent surface parameters that can be derived from the channel that measures the feature, "height," whereas the surface parameters in the second row represent surface parameters that can be derived from the channel that measures the feature, "adhesion." Note that a mnemonic device has been used to name the features, with all surface parameters that are derivable from the "height" channel beginning with "h" and all surface parameters that are derivable from the "adhesion" channel beginning with "a."

Thus, in the first row, the panel in the first column shows the importance coefficients for those surface parameters that are derived from the "height" channel when the machine-learning module 84 uses the Random Forest Method; the panel in the second column shows the importance coefficients for those surface parameters that are derived from the "height" channel when the machine-learning module 84 uses the Extremely Randomized Forest Method; and the panel in the third column shows the importance coefficients for those surface parameters that are derived from the "height" channel when the machine-learning module 84 uses the Method of Gradient Boosting Trees.

Similarly, in the second row, the panel in the first column shows the importance coefficients for those surface parameters that are derived from the "adhesion" channel when the machine-learning module 84 uses the Random Forest Method; the panel in the second column shows the importance coefficients for those surface parameters that are derived from the "adhesion" channel when the machine-learning module 84 uses the Extremely Randomized Forest Method; and the panel in the third column shows the importance coefficients for those surface parameters that are derived from the "adhesion" channel when the machine-learning module 84 uses the Method of Gradient Boosting Trees.

The histograms in FIG. 9 provide an intelligent way to choose those surface parameters that would be most helpful in correctly classifying a sample. For example, if the machine-learning module 84 were forced to choose only two surface parameters from the channel that measures height, it would probably avoid choosing "h_Sy" and "h_Std" but might instead prefer to choose "h_Ssc" and "h_Sfd."

The importance coefficients in FIG. 9 were arrived at using between a hundred trees and three hundred trees. The maximum number of elements in the chosen subset of original surface parameters was the square root of the number of surface parameters originally provided and the Gini index provided the basis for evaluating classification error. It is apparent from comparing the histograms in the same row that the choice of machine-learning procedure does not make a great deal of difference to the importance of particular surface parameters.

Figure 10:
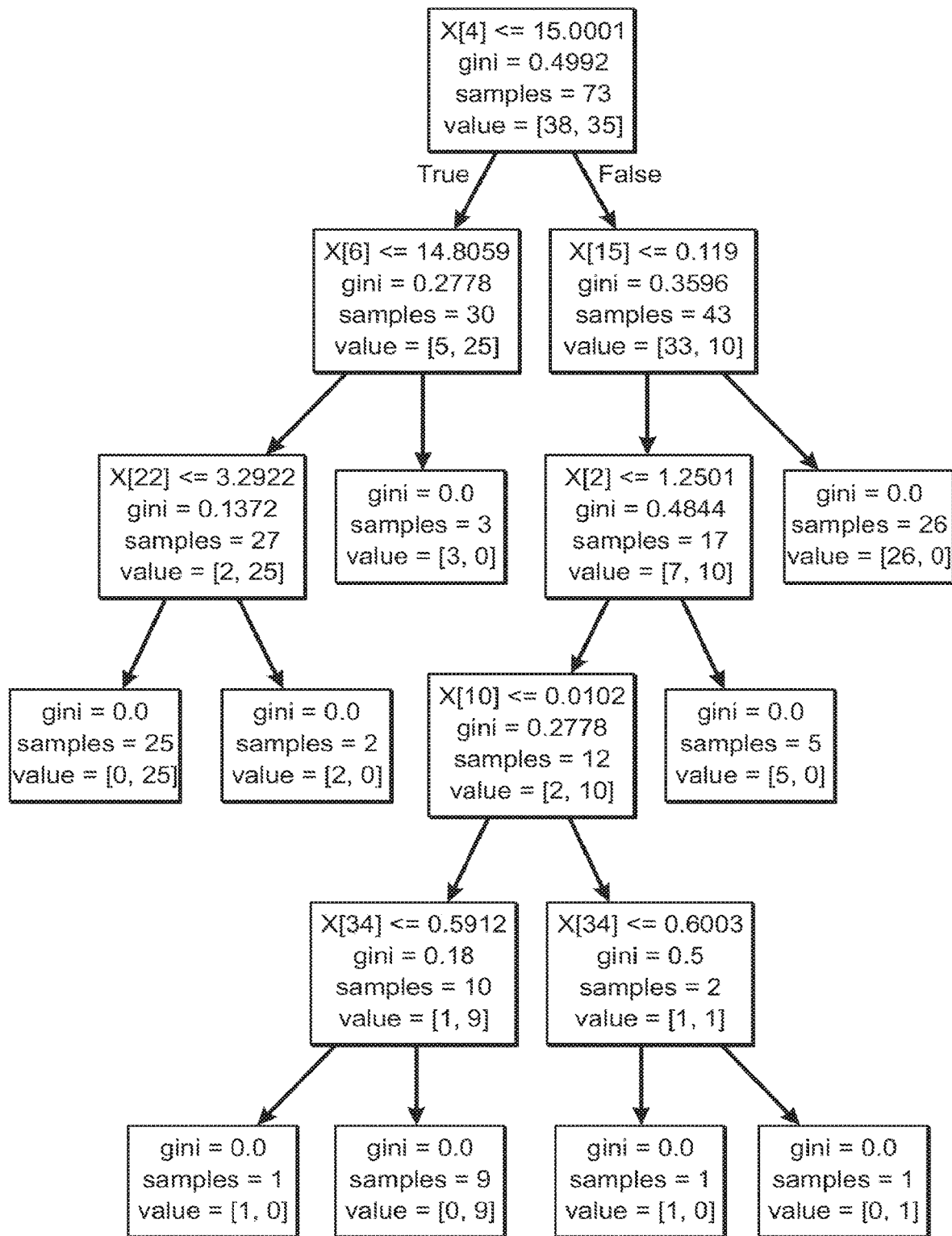
FIG. 10 shows a binary tree.

FIG. 10 shows an example of a binary tree from an ensemble of one hundred to three hundred trees used in the bootstrap methods. In the first split, the fourth variable "X[4]" was chosen with a split value of 15.0001. This yielded the Gini index of 0.4992 and split seventy-three samples into two bins having thirty and forty-three samples, respectively.

At the second level split, looking at left hand side node, the sixth variable "X[6]" was chosen with split value of 14.8059, which yielded the Gini index of 0.2778 and split thirty samples (five in class 1 and twenty-five in class 2) into two bins with twenty seven and three samples, respectively. The split continues until a tree node has the Gini index of zero, thus indicating presence of only one of the two classes.

The method of Extremely Randomized Trees differs from that of the Random Forest in its choice of the split. Instead of computing an optimal parameter and split combination using a Gini index, as was the case for the Random Forest method, a machine-learning module 84 using the method of Extremely Randomized Trees randomly selects each parameter value from the parameter empirical range. To ensure that these random choices eventually converge to a pure node with a zero Gini index, the machine-learning module 84 only chooses the best split among random uniform splits in the set of selected variables for which the current tree is chosen.

In some practices, the machine-learning module 84 implements the method of Gradient Boosting Trees. In this case, the machine-learning module 84 builds a series of trees, each of which converges with respect to some cost function. The machine-learning module 84 builds each subsequent tree to minimize the deviation from the exact prediction, for example by minimizing a mean squared error. In some cases, the machine-learning module 84 relies on the Friedman process for this type of regression. A suitable implementation of this regression process can be carried out using the routine "TREEBOOST" as implemented in the "SCIKIT-LEARN PYTHON" package.

Because the method of Gradient Boosting Trees lacks a criterion for pure nodes, the machine-learning module 84 predefines the size of the tree. Alternatively, the machine-learning module 84 limits the number of individual regressions, thus limiting the maximum depth of a tree.

A difficult that arises is that trees built with predefined sizes can easily be overfitted. To minimize the effect of this difficulty, it is preferable that the machine-learning module 84 impose constraints on such quantities as the number of boosting iterations or that it weaken the iteration rate, for example by using a dimensionless learning rate parameter. In alternative practices, the machine-learning module 84 limits the minimum number of terminal nodes, or leaves, on a tree.

In the implementations described herein, which relied on the SCIKIT-LEARN PYTHON package, the machine-learning module 84 set the minimum number of leaves to unity and the maximum depth to three. In the application described herein in which bladder cells collected from human subjects were to be classified, the machine-learning module 84 throttled back on its ability to learn by deliberating selecting an unusually low learning rate of 0.01. The resulting slow learning procedure decreases variance that resulted from having a small number of human subjects, and hence a small number of samples.

In creating the training data 87 and the testing data 89, it is important to avoid dividing the sets $\{M^{(k;1;p)}, M^{(k;2;p)} \ldots M^{(k;S;p)}\}$ between the training data 87 and testing data 89. The procedure disclosed in FIG. 11 avoids this.

Figure 12:
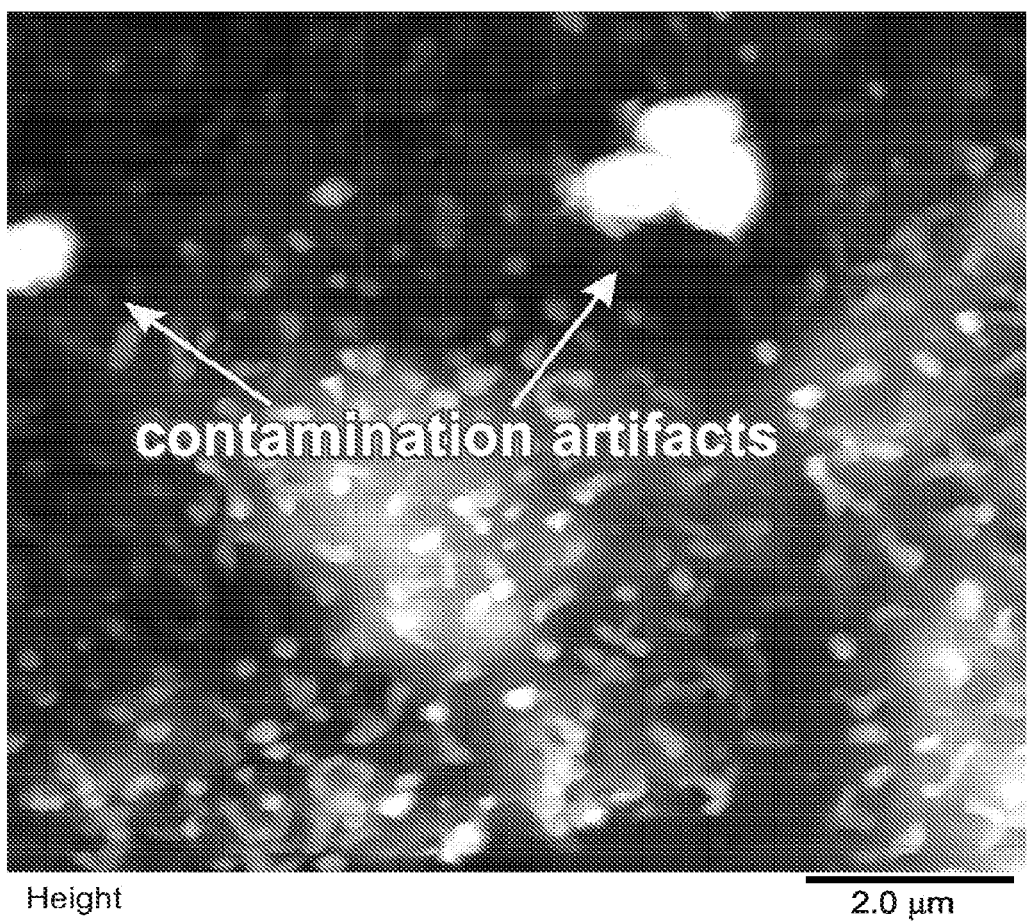
FIG. 12 shows a representative example of the artifacts because of possible contamination of the cell surface.

In the particular implementation of classifying bladder cells 90, each patient provided several cells, with the image of each cell 90 being divided into four partitions. A human observer visually inspected the partitions in an effort to spot artifacts, two of which can be seen in FIG. 12. If an artifact was found to be present in a partition, then whoever inspected the image would flag that partition as one that is to be ignored.

This process can become tedious when many cells 90 are involved. One can automate this process by using the classifier 100 shown in equation (10) and taking the median of the four partitions. This significantly dilutes the contribution of the artifact.

The machine-learning module 84 randomly splits the database 86 so that S % of its data is in the training data 87 and 100-S % is in the testing data 98. Experiments were carried out with S set to 50%, 60%, and 70%. The machine-learning module 84 split the database 86 in such a way as to keep data from the same individual entirely in either the training data 87 or the testing data 98 to avoid artificial over-training that may otherwise result from correlation between different cells 90 of the same individual.

The machine-learning module 84 then causes the condenser 104 to further reduce the number of surface parameters to be relied upon for classification. In some practices, the condenser 104 does so by ranking surface parameters within a particular channel based on their respective Gini indices and keeping some number $M_p$ of the best parameters for that channel. In some practices, the best parameters are selected based on their ability to their segregation power and their low correlation with other surface parameters. For example, by changing the inter-parameter correlation threshold, it becomes possible to change the number of surface parameters that will be relied upon for classification.

Figure 13:
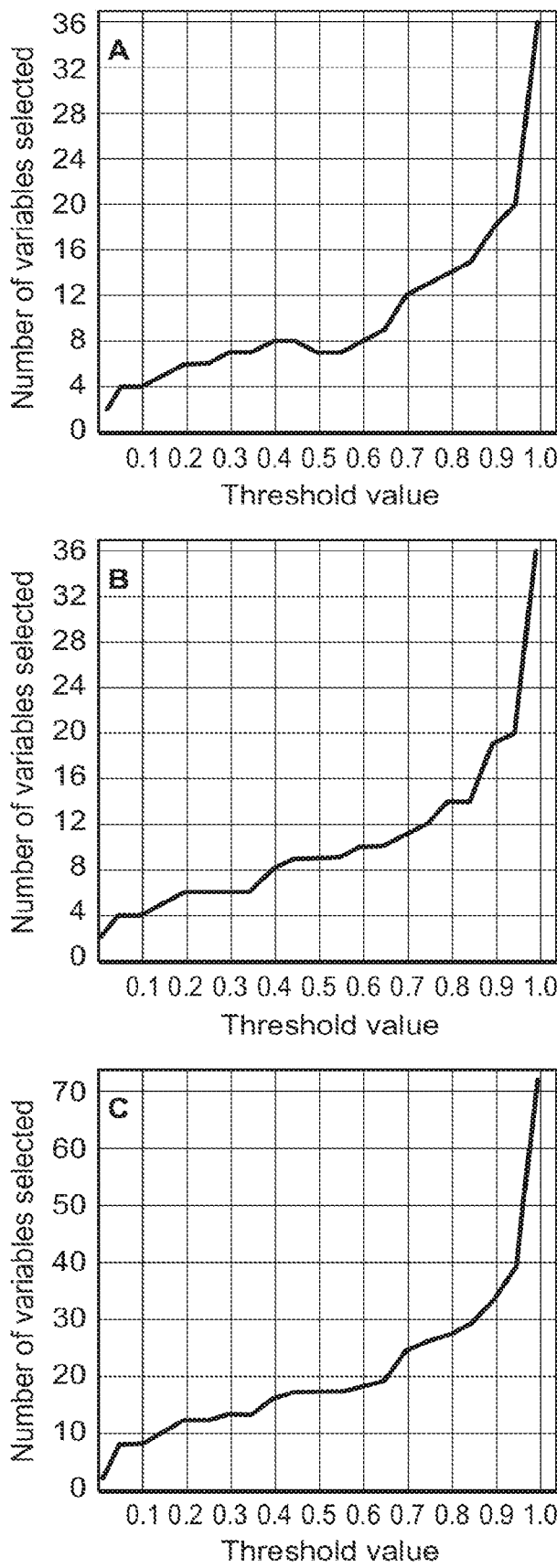
FIG. 13 shows the dependences of the number of surface parameters on the correlation threshold.

FIG. 13 shows how changing the threshold value of the correlation coefficient affects the number of surface parameters selected using the Random Forest Method, with the leftmost panel corresponding to the surface parameters available from the height channel and the middle panel corresponding to the surface parameters available from the adhesion channel. As is apparent from the change to the vertical scale, the rightmost panel represents the combination of the height channel and the adhesion channel. Although FIG. 13 is specific to the Random Forest Method, the other methods have similar curves.

Once the trees have been trained, it is appropriate to test their ability to classify correctly on the testing data 98 or alternatively, to use them to classify unknown samples. The classification process includes obtaining the result of tree voting and using that result as a basis for a probability indicative of what class a sample belongs to. This result is then compared with a classifier threshold that is set based on what error is tolerable. This classifier threshold is typically made to vary as part of building a receiver operating characteristic.

In one experiment, samples of urine 88 were collected from twenty-five cancer-afflicted patients and forty-three cancer-free patients. Of the cancer-afflicted patients, fourteen were low grade and eleven were high grade as defined by TURBT. The cancer-free patients were either healthy or had had cancer in the past. Using an optical microscope that was coupled to the atomic force microscope 8, a human observer randomly selected round objects that appeared to be cells.

The database was further reduced by using the data-reduction process referred to in equation (14). The resulting probably generator 100 was therefore $P_{nm}^{(k;s)}$=median $\{P_{mn}^{(k;s;p)}\}$ where p is an integer between 1 and 4 inclusive to correspond with the four partitions of each image. The resulting condensed database has two classes and can be formally represented as:

$$D_1^{(1;s)}=\{P_1^{(k;s)}{}_m,C^{(1)}\}, D_2^{(1;s)}=\{P_2^{(k;s)}{}_m,C^{(1)}\} \ldots$$
$$D_{Ndata1}^{(1;s)}=\{P_{Ndata1}^{(k;s;p)}{}_m,C^{(1)}\} D_1^{(2;s)}=$$
$$\{P_1^{(k;s)}{}_m,C^{(2)}\}, D_2^{(2;s)}=\{P_2^{(k;s)}{}_m,C^{(2)}\} \ldots$$
$$D_{Ndata2}^{(2;s)}=\{P_{Ndata1}^{(k;s)}{}_m,C^{(2)}\}, \quad (3)$$

At least five cells were imaged per patient. For the sake of simplicity only two properties were considered: height and adhesion.

Figure 14:
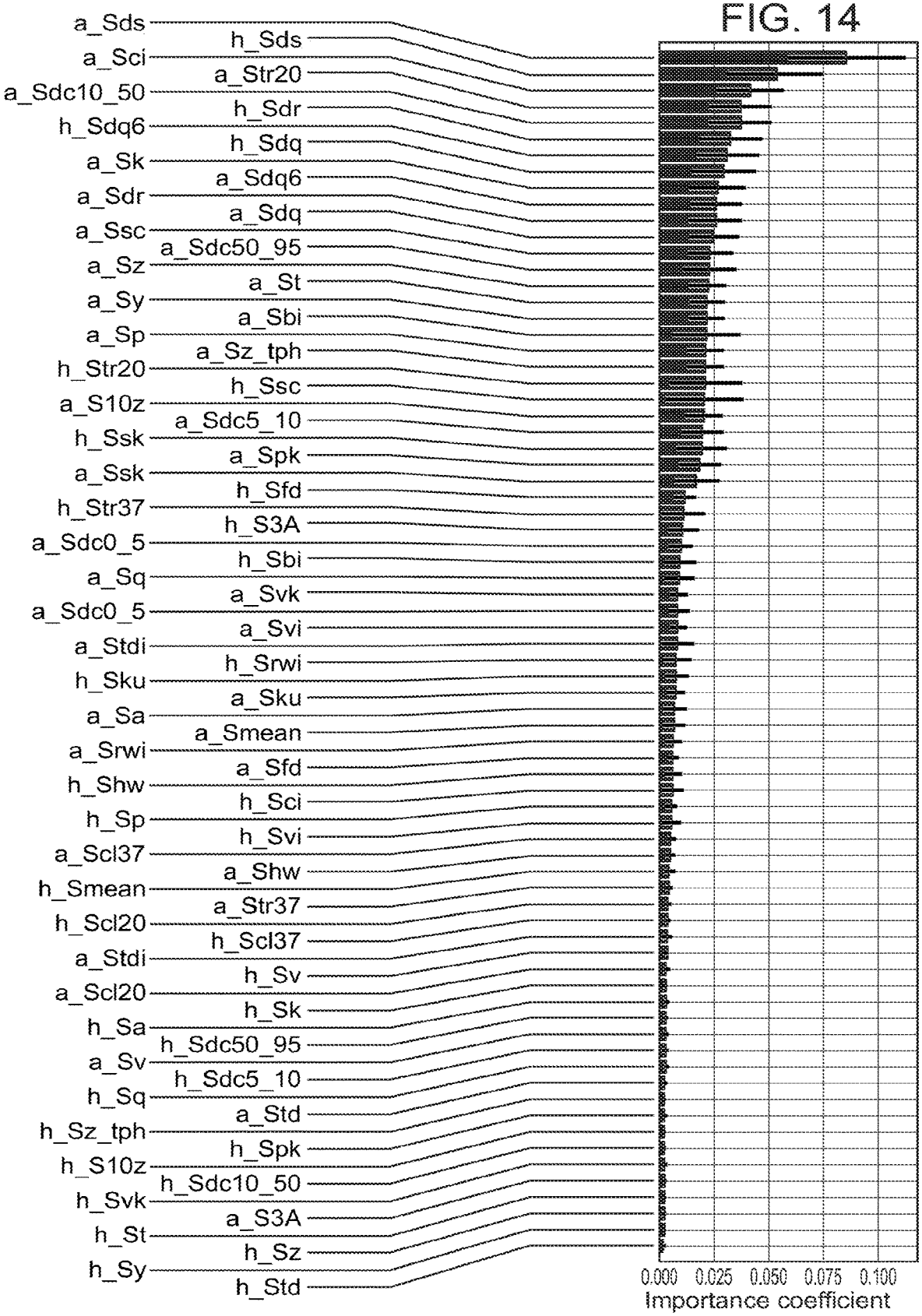
FIG. 14 shows the hierarchy of importance of the surface parameters for height and adhesion properties calculated within the Random Forest method.

FIG. 14 shows the hierarchy of importance of the surface parameters for height and adhesion properties calculated within the Random Forest method. The figure shows the averages of the importance coefficients together with an error bar indicating one standard deviation about the average. The database 86 was randomly split into training data 87 and testing data 89 a thousand times.

The mapped properties for height and adhesion were combined through tensor addition, which is basically the data-reduction method (3-1) adapted for vectors of surface parameters). The relevant tensor addition operation is represented by:

$$P_{nm}^{(1;s)} \oplus P_{nm}^{(2;s)}$$

As was the case in FIG. 9, each surface parameter in FIG. 14 has, as its name, the standard name of the surface parameter but prepending by a letter indicating the mapped property from which it was derived. For example, "a_Sds" means the "Sds" parameter derived from an image of adhesion property.

A suitable statistical performance metric for the Random Forest method comes from inspecting the receiver operating characteristic and the confusion matrix. The receiver operating characteristic permits defining range of sensitivity and specificity. The range of sensitivity corresponds to "accuracy" when classifying a cell as coming from a cancer-afflicted patient, whereas specificity corresponds to "accuracy" when the cell is classified as from a cancer-free person. The receiver operating characteristic makes it possible to use the receiver operating characteristic to define a range of specificity and a range of sensitivity, as follows:

sensitivity=TP/(TP+FN);

specificity=TN/(TN+FP);

accuracy=(TN+TP)/(TP+FN+TN+FP), (19)

where TN, TP, FP, FN stand for true negative, true positive, false positive, and false negative, respectively.

Figure 15:
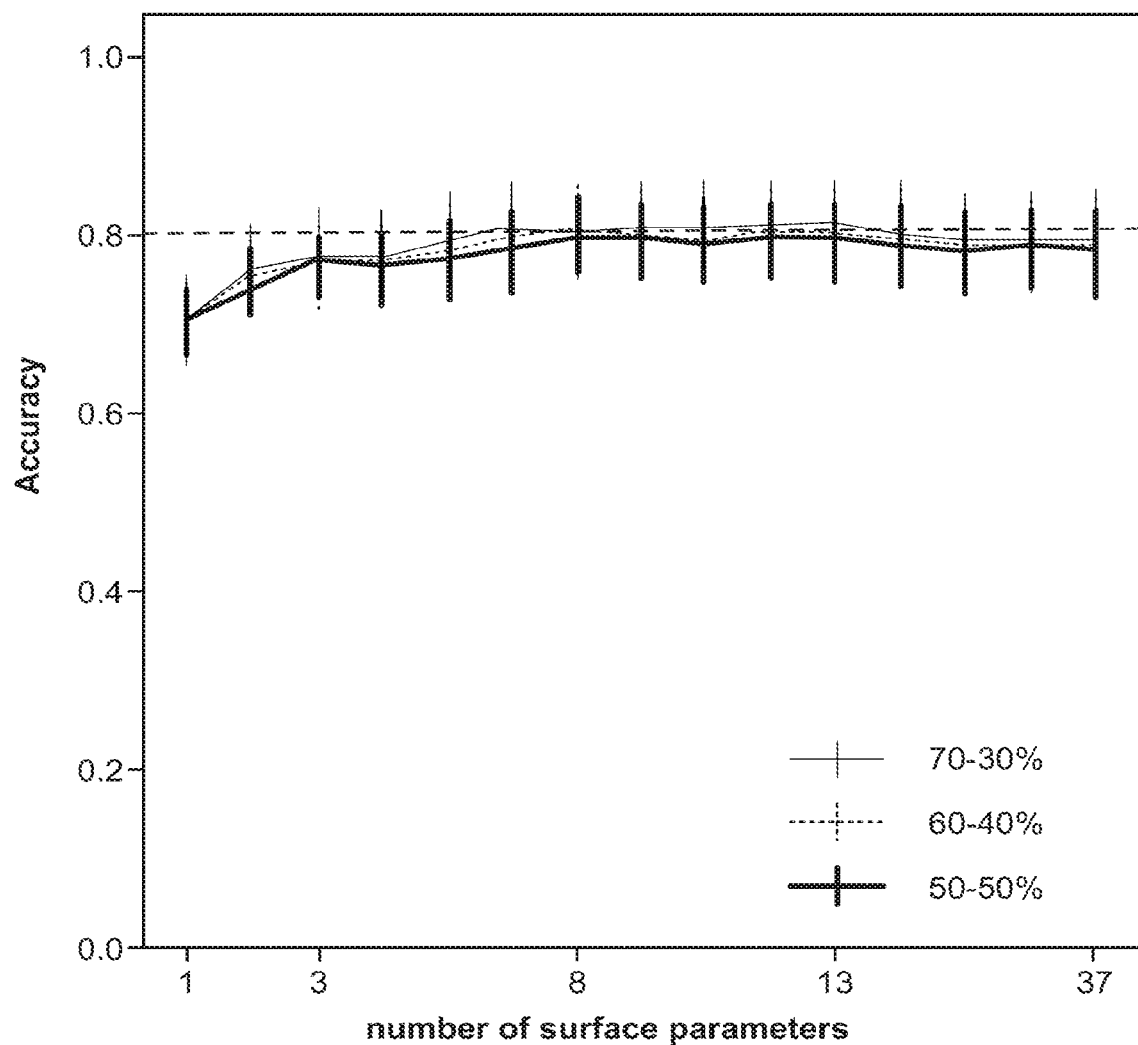
FIG. 15 shows accuracy for different numbers of surface parameters and different allocations of data among the training and testing database as calculated using the Random Forest method for combined channels of height and adhesion.

FIG. 15 shows three different curves, each of which shows the accuracy achieved by considering different numbers of surface parameters, wherein the surface parameters were chosen based choosing different self-correlation thresholds and importance coefficients as described above.

Each of the three different curves in FIG. 15 was arrived at through a thousand random splits between training data 87 and testing data 89. The curves differ in the allocation of data to each set. A first curve corresponds to 70% of the data being allocated to the training data 87 and 30% being allocated to the testing data 89. A second curve corresponds to only 60% of the data being allocated to training data 87 and 40% being allocated to the testing data 89. And a third curve corresponds to an even split between training data 87 and testing data 89.

It is apparent from inspection of FIG. 15 that there is virtually no dependence on a particular threshold split. This indicates robustness of the procedure carried out by the machine-learning module 84.

Figure 16:
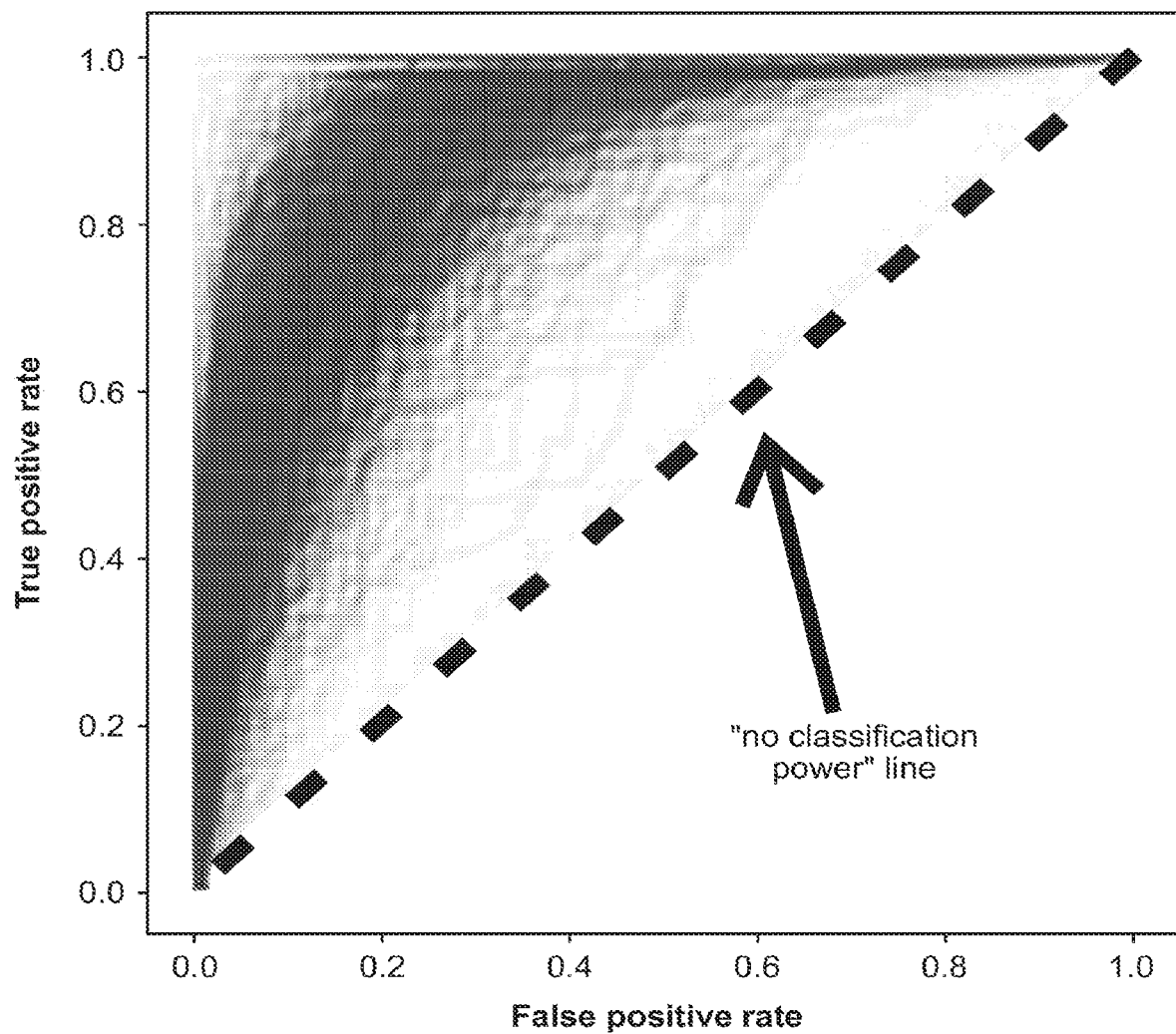
FIG. 16 shows receiver operating characteristics using the Random Forest method for the combined channels of height and adhesion.

FIG. 16 shows a family of receiver operating characteristics. The individual receiver operating characteristic in the family of characteristics shown in FIG. 16 arose from two hundred different random splits of the database 86 into training data 87 and testing data 89.

Each receiver operating characteristic shows sensitivity and specificity for different thresholds when attempting to classify between two classes. The diagonal line that bisects the plot in FIG. 16 amounts to a classifier that classifies by flipping a coin. Thus, the closer a receiver operating characteristic comes to the diagonal line shown in FIG. 16, the poorer its classifier is at classifying. The fact that the curves are clustered far from this diagonal line with little variation between individual curves suggests both the effectiveness of the classifier and its insensitivity to the specific choice of training data 87 and testing data 89.

In constructing a receiver operating characteristic, the threshold that defines whether a particular probability value corresponds to one class or the other is a free parameter. The choice of this parameter governs both specificity and sensitivity. For each receiver operating characteristic, there exists a point that corresponds to the minimum error in classifying a sample that should have been in the first class into the second class and vice versa. This is shown in FIG. 21 for each of the three machine-learning methods used when using a single channel.

Each row in the table shown in FIG. 21 is characterized by a particular number of collected cells (N) and a smaller number (M) that was used as a threshold for diagnosis. For each row, there were two channels considered: height and adhesion. For each of the three machine-learning methods used, the table shows the averaged AUC and accuracy for a thousand random splits of the database into training data and testing data with 70% of the database being allocated to the training data. The accuracy is that associated with the smallest error in classification. Each row in FIG. 21 also shows sensitivity and specificity.

In principle, the sensitivity and specificity can also be defined around a balanced point in which sensitivity and specificity are equal. Because of a limited number of human subjects, it is difficult to define precisely where this balanced point would be. Thus, in FIG. 21, the requirement for equality was relaxed and a balance range was defined in which the magnitude of the difference between sensitivity and specificity had to be less than a selected value, which for FIG. 21 was 5%.

Only ten surface parameters were used to calculate the receiver operating characteristic. As was apparent from FIG. 15, there is a point of diminishing returns at which adding more surface parameters does not significantly improve accuracy. According to FIG. 15, it is apparently sufficient to use only eight to ten judiciously chosen surface parameters to achieve a relatively high accuracy of 80%. The top ten surface parameters were considered to characterize the statistical behavior of the receiver operating characteristic and the confusion matrix, including the specificity, sensitivity, and accuracy of the classifier 100.

The process of classifying a cell as having come from a cancer-free patient or a cancer-afflicted patient relies on averaging the probability obtained for that cell over all repetitions of the procedure used to acquire that probability. This is formally represented as:

$$Prob_n^{(l)} = \frac{1}{S}\sum_s Prob_n^{(s)(l)}, \quad (20)$$

where $$Prob_n^{(s)(l)} = AI\big(P_{nm}^{(1,s)} \oplus P_{nm}^{(2,s)} \mid C^{(l)}\big),$$

where the classifier AI was developed using the machine learning methods developed on the training database 87. According to this procedure, and assuming class 1 represents a cancer cell, a cell is identified as having come from a cancer-afflicted patient if $Prob_n^{(1)}$ exceeds a particular threshold, which can be obtained from the receiver operating characteristic.

Figure 17:
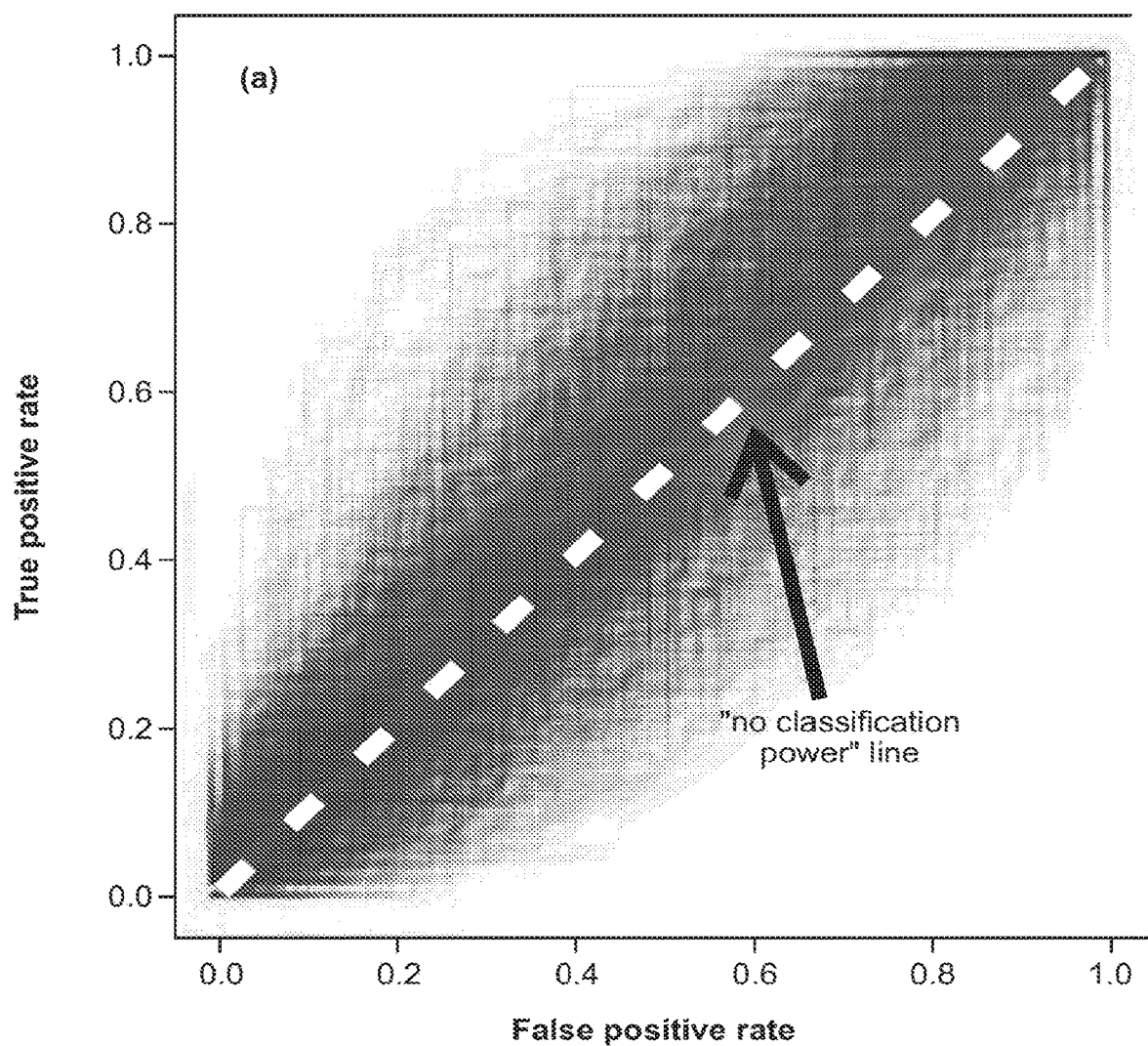
FIG. 17 shows a plot similar to that shown in FIG. 16 but with artificial data used to confirm the reliability of the procedure used to generate the data in FIG. 16.
Figure 18:
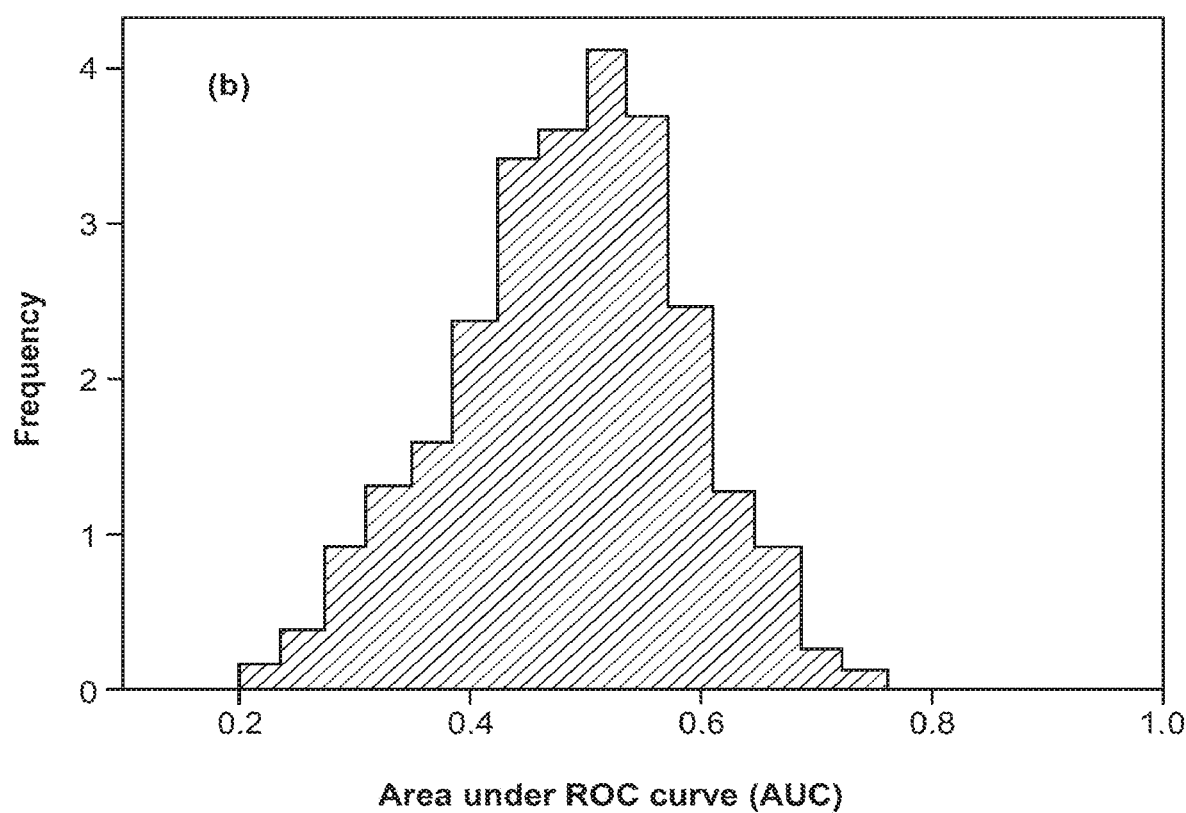
FIG. 18 shows area under the receiver operating characteristics of FIG. 17.
Figure 19:
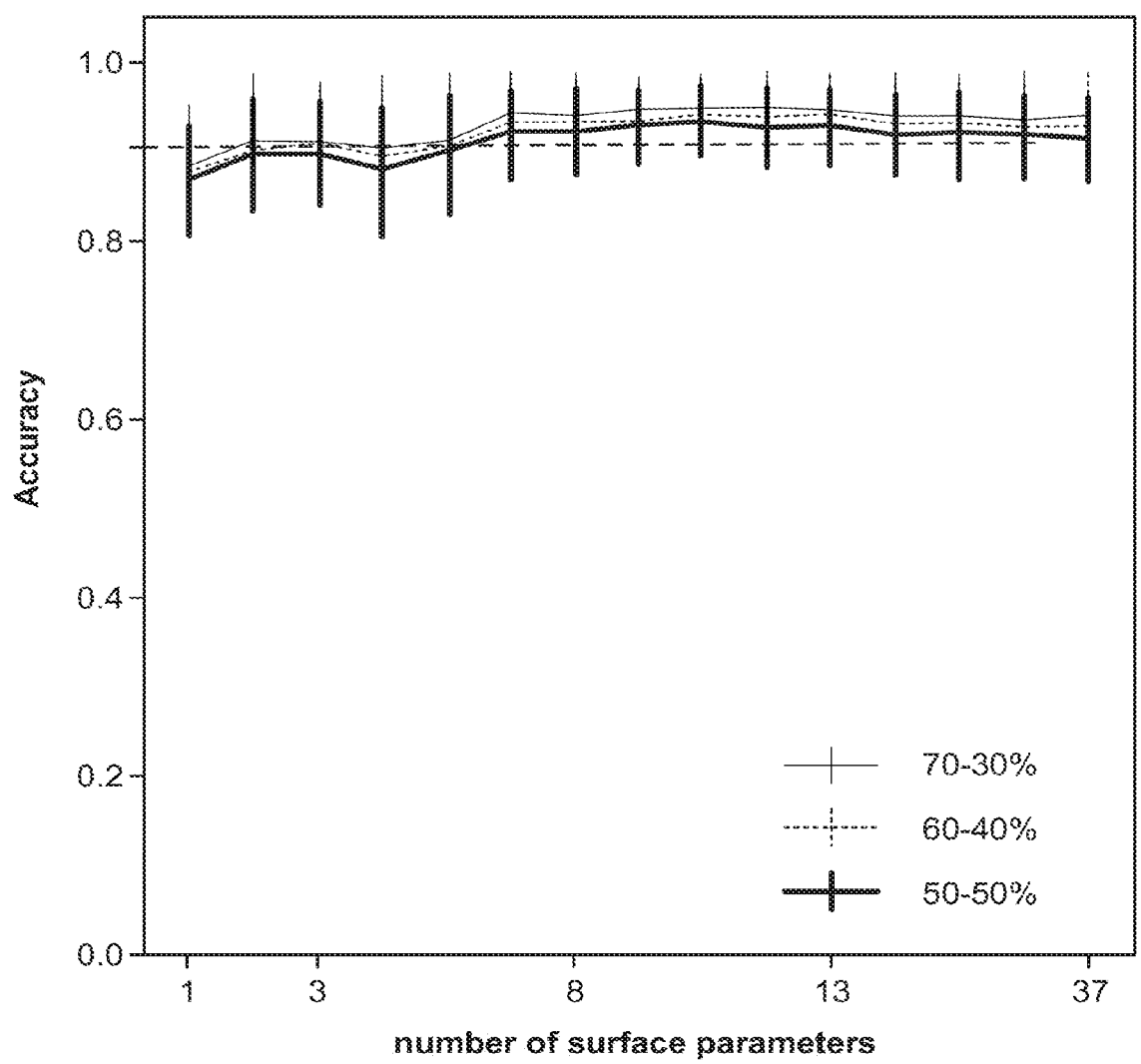
FIG. 19 shows accuracy for different numbers of surface parameters and different ways of allocating data between the training data and testing data using the Random Forest method for the combined channels of height and adhesion when using with five cells per patient and two cells required to be identified as having come from a cancer-afflicted patient (N=5, M=2)
Figure 20:
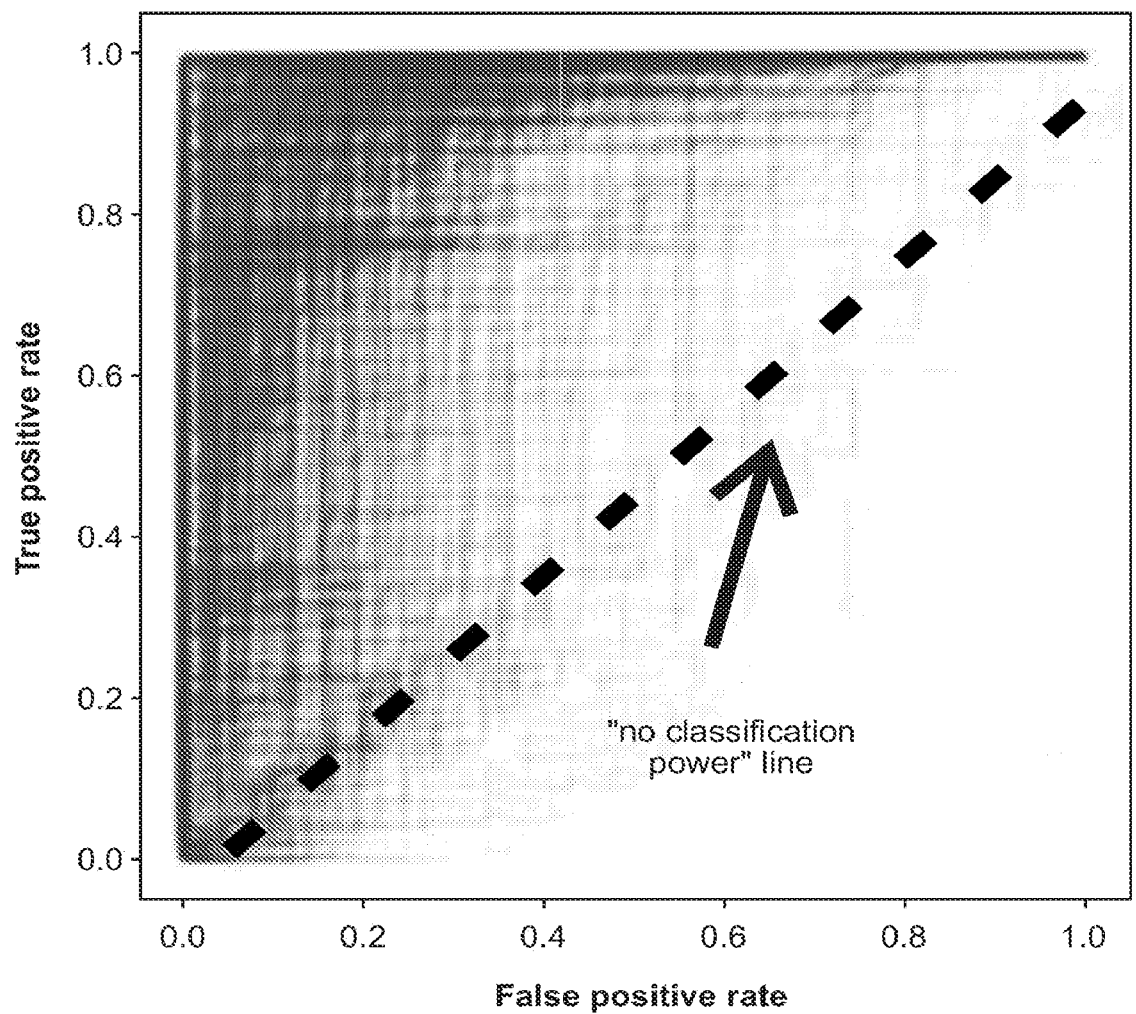
FIG. 20 shows receiver operating characteristics calculated using the Random Forest method for the combined channels of height and adhesion when using with five cells per patient and with two cells required to be identified as having come from a cancer-afflicted patient (N=5, M=2)

In an effort to confirm the veracity of the data shown in FIGS. 18 and 19, a control experiment was carried out with the same procedure as was used for FIGS. 19 and 20 but with the samples to be classified having been split evenly between cancer cells and healthy cells. FIGS. 17 and 18 show the result of a thousand random choices of classification. It is apparent that the accuracy has dropped to 53%±10%, which is consistent with expectations. This suggests the reliability of the data shown in FIGS. 19 and 20 as well as the classifier's resistance to overtraining, which is a common problem that arises when a machine-learning method is made to cope with too many parameters.

An alternative method of classification relies on more than one cell to establish a diagnosis of a patient. This avoids a lack of robustness based on a high sampling error. Moreover, this avoids error that arises because one cannot be sure that a cell found in urine 88 is actually from the bladder itself. Other parts of the urinary tract are perfectly capable of shedding cells. In addition, urine 88 can contain an assortment of other cells, such as exfoliated epithelial cells from other parts of urinary tract. One such classification method includes diagnosing a patient with cancer if the number of cells M classified as having come from a cancer-afflicted patient out of the total number of cells classified N is greater or equal to a predefined value. This is a generalization of the previously discussed case in which N=M=1.

The probability of having cancer based on probabilities for N cells can be assigned using algorithms (3-2)-(3-9) or (10)-(14). As a preferable procedure to define the probability of classifying the N tested cells as coming from a cancer patient (Class 1) is as follows:

$$Prob_n^{(1)} = \underset{s=1...N}{\text{Max}} \{Prob_n^{(s)(1)}\} \quad (21)$$

where $$Prob_n^{(s)(1)} = AI(P_{nm}^{(1,s)} \oplus P_{nm}^{(2,s)} \mid C^{(1)}),$$

where the classifier AI is developed from the training database 87.

FIGS. 19 and 20 show accuracy and receiver operating characteristics similar robustness to those in FIGS. 15 and 16 but for the case of N=5 and M=2. One can see that the accuracy of such method can reach 94%. The randomization test described above shows 50±22% for the area under receiver operating characteristic curves (the result of a thousand random choices of diagnosis sets). These imply the lack of overtraining.

The results of calculation of the confusion matrix for multiple N and M are shown in FIG. 20 table exampled for two single channels (height and adhesion). The robustness of combined channels is better compared to the diagnostic based on single channels.

The procedure described above can also be applied to classify cancer free patients. In such a case, the probabilities discussed above are the probabilities that the cell belongs to a cancer free patient.

Having described the invention and a preferred embodiment thereof, what is claimed as new and secured by Letters Patent is:

1. An apparatus for detecting bladder cancer in a patient, the apparatus comprising:
   an atomic force microscope comprising a probe, wherein the probe is configured to scan a first surface of a first bladder cell and
   a processing system configured to acquire a first image of the first surface from the atomic force microscope, to compare the first image to a second image, the second image being that of a second surface of a second bladder cell, the second bladder cell being a bladder-cancer cell, and to classify the first bladder cell as also being a bladder-cancer cell.

2. The apparatus of claim 1, wherein the first bladder cell is obtained from a urine sample of the patient.

3. The apparatus of claim 1, wherein the atomic force microscope is configured to scan the first surface in ringing mode.

4. The apparatus of claim 1, wherein the atomic force microscope is configured to scan the first surface in a sub-resonance tapping mode.

5. The apparatus of claim 1, wherein said processing system comprises a machine-learning module and a classifier, wherein said classifier is configured to classify said first bladder cell after having learned a basis for classification from said machine-learning module.

6. The apparatus of claim 1, wherein said processing system comprises a machine-learning module and wherein said processing system is configured to process said images to obtain surface parameters and to use said machine-learning module to classify said surfaces based at least in part on said surface parameters.

7. The apparatus of claim 1, wherein said atomic-force microscope comprises a multi-channel atomic force microscope, each channel of which corresponds to a surface property of said surfaces.

8. The apparatus of claim 1, wherein said processing system comprises a condenser that condenses information provided by channels provided by said atomic-force microscope, each of said channels corresponding to a surface property of said surface, and wherein said condenser is further configured to construct, from said condensed information, a condensed database.

9. The apparatus of claim 1, further comprising a classifier that classifies said first bladder sample based on a condensed database, said condensed database containing condensed information provided by channels provided by said atomic-force microscope, each of each of said channels corresponding to a surface property of said surface.

10. The apparatus of claim 1, further comprising a condenser that condenses information provided by channels provided by said atomic-force microscope, each of said channels corresponding to a surface property of surfaces of bladder cells to construct a condensed database, wherein said condenser is configured to construct said condensed database by projecting a first database of bladder cell surface properties into a subspace of dimensionality lower than that of said first database, said projection defining said condensed database, said condensed database having a dimensionality that is less than that of said first database.

11. The apparatus of claim 1, wherein said processing system comprises a machine-learning module and a classifier, wherein said classifier is configured to classify said first bladder cell after having learned a basis for classification from said machine-learning module, wherein said machine-learning module has been trained with training data and tested using testing data, said training data having been used to learn how to classify bladder cells and said testing data having been used to verify that a classification of bladder cell learned based on said training data is effective enough to pass a given threshold of effectiveness for detection of bladder cancer.

* * * * *